US011418700B2

(12) United States Patent
Tamonoki

(10) Patent No.: US 11,418,700 B2
(45) Date of Patent: Aug. 16, 2022

(54) CONTROL DEVICE, ENDOSCOPE SYSTEM, PROCESSING METHOD, AND PROGRAM

(71) Applicant: Sony Olympus Medical Solutions Inc., Tokyo (JP)

(72) Inventor: Sadayuki Tamonoki, Tokyo (JP)

(73) Assignee: SONY OLYMPUS MEDICAL SOLUTIONS INC., Tokyo (JP)

( * ) Notice: Subject to any disclaimer, the term of this patent is extended or adjusted under 35 U.S.C. 154(b) by 0 days.

(21) Appl. No.: 16/492,948

(22) PCT Filed: Dec. 11, 2017

(86) PCT No.: PCT/JP2017/044442
§ 371 (c)(1),
(2) Date: Sep. 11, 2019

(87) PCT Pub. No.: WO2018/179610
PCT Pub. Date: Oct. 4, 2018

(65) Prior Publication Data
US 2020/0021746 A1 Jan. 16, 2020

(30) Foreign Application Priority Data
Mar. 27, 2017 (JP) .............................. JP2017-061831

(51) Int. Cl.
*A61B 1/00* (2006.01)
*A61B 1/04* (2006.01)
(Continued)

(52) U.S. Cl.
CPC ... *H04N 5/232127* (2018.08); *A61B 1/00009* (2013.01); *A61B 1/00048* (2013.01);
(Continued)

(58) Field of Classification Search
CPC ... A61B 1/00; A61B 1/00009; A61B 1/00048; A61B 1/00188; A61B 1/005; A61B 1/04;
(Continued)

(56) References Cited

U.S. PATENT DOCUMENTS

| 2002/0004626 A1* | 1/2002 | Abe | A61B 1/042 |
| | | | 600/109 |
| 2014/0037165 A1* | 2/2014 | King | A61B 5/748 |
| | | | 382/128 |

(Continued)

FOREIGN PATENT DOCUMENTS

| JP | 4-102437 A | 4/1992 |
| JP | 2005-124756 A | 5/2005 |

(Continued)

OTHER PUBLICATIONS

International Search Report and Written Opinion dated Mar. 6, 2018 for PCT/JP2017/044442 filed on Dec. 11, 2017, 13 pages including English Translation of the International Search Report.

*Primary Examiner* — Alison Slater
(74) *Attorney, Agent, or Firm* — Xsensus LLP

(57) ABSTRACT

Provided is a control device, an endoscope system, a processing method, and a program which can select a region other than the center region in an image to perform a predetermined process. An endoscope system includes an image generation unit which processes an image signal generated by an imaging unit to generate a display image to be displayed, a display controller which overlaps a plurality of select regions selectable according to an external operation to the display image and outputs the overlapped image to the display device, and an autofocus controller which performs a predetermined process on at least one select region selected according to the external operation.

23 Claims, 15 Drawing Sheets

(51) Int. Cl.
*A61B 1/05* (2006.01)
*H04N 5/232* (2006.01)
*H04N 5/225* (2006.01)

(52) U.S. Cl.
CPC ............ *A61B 1/00188* (2013.01); *A61B 1/04* (2013.01); *H04N 5/23216* (2013.01); *H04N 5/23296* (2013.01); *H04N 2005/2255* (2013.01)

(58) Field of Classification Search
CPC ......... A61B 1/045; A61B 1/06; A61B 90/361; A61B 1/0005; A61B 1/00006; A61B 1/3132; A61B 34/25; A61B 1/05; A61B 1/00011; A61B 1/00039; A61B 1/042; A61B 1/0002; A61B 1/00045; A61B 1/00059; A61B 2090/3612; A61B 5/0077; A61B 1/00057; A61B 1/00163; A61B 1/0019; A61B 1/043; A61B 1/0669; A61B 1/0676; A61B 1/0684; A61B 2034/256; A61B 5/0084; A61B 5/748; A61B 90/30; A61B 1/00016; A61B 1/00096; A61B 1/00117; A61B 1/00124; A61B 1/00149; A61B 1/041; A61B 1/051; A61B 2017/00216; A61B 2034/252; A61B 5/0059; A61B 5/0075; A61B 5/0095; A61B 5/024; A61B 5/1032; A61B 5/72; A61B 5/743; A61B 5/749; A61B 1/00013; A61B 1/00018; A61B 1/00029; A61B 1/00032; A61B 1/00036; A61B 1/00041; A61B 1/00062; A61B 1/00105; A61B 1/00108; A61B 1/00114; A61B 1/00128; A61B 1/00177; A61B 1/00186; A61B 1/00193; A61B 1/0051; A61B 1/0615; A61B 1/0623; A61B 1/0638; A61B 1/0653; A61B 1/0661; A61B 1/07; A61B 1/273; A61B 1/303; A61B 1/31; A61B 17/1285; A61B 2017/00199; A61B 2017/00477; A61B 2090/306; A61B 2090/372; A61B 2090/5025; A61B 2090/508; A61B 2560/0487; A61B 2562/0219; A61B 3/113; A61B 34/30; A61B 34/32; A61B 34/37; A61B 34/70; A61B 34/74; A61B 5/0071; A61B 5/055; A61B 5/062; A61B 5/1128; A61B 5/14556; A61B 5/1459; A61B 5/414; A61B 5/742; A61B 5/7425; A61B 5/7485; A61B 6/032; A61B 6/52; A61B 8/52; A61B 90/20; A61B 90/50; G02B 23/24; G02B 7/28; G02B 7/36; G03B 13/36; H04N 2005/2255; H04N 5/225; H04N 5/232; H04N 5/232127; H04N 5/23216; H04N 5/23296; H04N 5/235; H04N 7/183; H04N 5/23293; H04N 5/2256; H04N 5/2258; H04N 5/23232; H04N 5/23245; H04N 5/2351; H04N 7/147; H04N 5/2354; H04N 5/2252; H04N 5/2254; H04N 5/23209; H04N 5/23238; H04N 5/232935; H04N 5/232939; H04N 5/2353; H04N 5/265; H04N 5/345; H04N 7/18; H04N 9/04557; H04N 1/212; H04N 1/2141; H04N 21/234345; H04N 21/234363; H04N 21/2365; H04N 21/242; H04N 21/25825; H04N 21/440245; H04N 21/440263; H04N 21/4516; H04N 21/45455; H04N 21/816; H04N 21/8547; H04N 2101/00; H04N 2201/0079; H04N 5/04; H04N 5/147; H04N 5/2259; H04N 5/23203; H04N 5/23212; H04N 5/23219; H04N 5/23229; H04N 5/23235; H04N 5/23241; H04N 5/2352; H04N 5/335; H04N 5/341; H04N 5/343; H04N 5/3452; H04N 5/3454; H04N 5/3456; H04N 5/351; H04N 5/3532; H04N 5/365; H04N 5/367; H04N 5/378; H04N 5/45; H04N 5/765; H04N 5/77; H04N 5/772; H04N 7/181; H04N 9/0451; H04N 9/04511; H04N 9/04515; H04N 9/07; H04N 9/09; H04N 9/76; H04N 9/797; H04N 9/8042

See application file for complete search history.

(56) References Cited

U.S. PATENT DOCUMENTS

| | | | |
|---|---|---|---|
| 2014/0187856 A1* | 7/2014 | Holoien | A61B 1/0005 600/103 |
| 2015/0381879 A1* | 12/2015 | Sato | H04N 5/23209 348/207.11 |
| 2016/0000300 A1* | 1/2016 | Williams | A61B 1/05 600/109 |
| 2016/0015247 A1* | 1/2016 | Irion | A61B 1/00057 356/432 |
| 2016/0234427 A1* | 8/2016 | Yoshino | A61B 1/00036 |
| 2017/0023492 A1* | 1/2017 | Olsson | G03B 37/005 |
| 2017/0100019 A1* | 4/2017 | Ikuma | G02B 23/2484 |
| 2018/0109727 A1* | 4/2018 | Tamai | H04N 21/440245 |
| 2018/0296067 A1* | 10/2018 | Amling | A61B 1/00016 |
| 2018/0307933 A1* | 10/2018 | Iwaki | A61B 1/04 |
| 2019/0219831 A1* | 7/2019 | Duckett | A61B 1/042 |
| 2019/0260929 A1* | 8/2019 | Kaneko | H04N 5/23238 |
| 2019/0394395 A1* | 12/2019 | Kamiya | G03B 13/02 |
| 2020/0128214 A1* | 4/2020 | Tsuchiya | A61B 1/00009 |

FOREIGN PATENT DOCUMENTS

| | | |
|---|---|---|
| JP | 2009-519764 A | 5/2009 |
| JP | 2012-115554 A | 6/2012 |
| JP | 2014-175965 A | 9/2014 |
| JP | 2015-228955 A | 12/2015 |
| JP | 2017-000568 A | 1/2017 |
| JP | 2017-12553 A | 1/2017 |
| WO | 2015/151543 A1 | 10/2015 |
| WO | WO-2017006933 A1 | 1/2017 |
| WO | WO-2018235389 A1 * | 12/2018 ............. A61B 1/045 |

* cited by examiner

CONTROL DEVICE, ENDOSCOPE SYSTEM, PROCESSING METHOD, AND PROGRAM

CROSS-REFERENCE TO RELATED APPLICATIONS

The present application is based on PCT filing PCT/JP2017/044442, filed Dec. 11, 2017, which claims priority to JP 2017-061831, filed Mar. 27, 2017, the entire contents of each are incorporated herein by reference.

TECHNICAL FIELD

The present invention relates to a control device, an endoscope system, a processing method, and a program in which a subject is captured and image data of the subject is processed.

BACKGROUND ART

In recent years, there is known a technique in which an endoscope can perform an auto focus (AF) process to adjust focusing automatically (see Patent Literature 1). In the technique, a focus evaluation is calculated based on an image capture signal generated by an imaging unit, and the driving of a focus mechanism is controlled according to the calculation result, so that the center region of the image corresponding to the image capture signal is in focus.

CITATION LIST

Patent Literature

Patent Literature 1: JP 2017-568 A

DISCLOSURE OF INVENTION

Technical Problem

However, in Patent Literature 1, the processing region is fixed to the center region. Therefore, even in a case where a user wants to perform an AF process on another region or various processes which are executable in the endoscope, the user is not able to select the other region.

The invention has been made in view of the above problem, and an object thereof is to provide a control device, an endoscope system, a processing method, and a program which can select a region other than the center region in an image to perform a predetermined process.

Solution to Problem

To solve the above-described problem and achieve the object, a control device according to the present invention includes: an image generation unit configured to process an image signal generated by an imaging unit to generate a display image to be displayed; a display controller configured to overlap a plurality of select regions selectable according to an external operation and output the overlapped image to a display device; and a control unit configured to perform a predetermined process on at least one select region selected according to the external operation.

Moreover, in the above-described control device according to the present invention, the control unit is configured to control driving of a lens unit which includes a focus mechanism configured to move one or a plurality of lenses to adjust focusing so as to make the lens unit focused on at least one select region selected according to the external operation.

Moreover, the above-described control device according to the present invention further includes an electronic zoom unit configured to perform a trimming process on a predetermined region in the display image to generate a magnification image, wherein the control unit is configured to cause the electronic zoom unit to perform a trimming process on at least one select region selected according to the external operation to generate the magnification image.

Moreover, the above-described control device according to the present invention further includes a brightness detector configured to detect a brightness of an illumination light emitted from a light source device based on a pixel value of a predetermined region in the display image to generate a light control signal to adjust the light source device, wherein the control unit is configured to cause the brightness detector to detect a brightness of the illumination light with respect to at least one select region selected according to the external operation to generate the light control signal.

Moreover, the above-described control device according to the present invention further includes a detection unit configured to detect a type of an endoscope connected to the control device, wherein the display controller is configured to change display sizes of the plurality of select regions based on the type of the endoscope detected by the detection unit and overlaps the select regions to the display image.

Moreover, in the above-described control device according to the present invention, the detection unit detects the type of the endoscope based on a boundary between a subject image and a mask region in the display image.

Moreover, the above-described control device according to the present invention further includes an operating unit configured to output a select signal to select any one of the plurality of select regions, wherein the display controller is configured to highlight the select region which is selected according to the select signal output from the operating unit.

Moreover, in the above-described control device according to the present invention, the display controller is configured to transition the select region to another select region and highlight the select region whenever the operating unit outputs the select signal.

Moreover, in the above-described control device according to the present invention, the operating unit is provided rotatably about a predetermined axis, and is configured to output the select signal at each predetermined rotation angle.

Moreover, an endoscope system according to the present invention includes: an endoscope configured to be inserted in a subject; an imaging unit configured to receive a subject image formed by the endoscope to perform a photoelectric conversion; an image generation unit configured to process the image signal generated by the imaging unit to generate a display image; a display device configured to display the display image generated by the image generation unit; a display controller configured to overlap a plurality of select regions selectable according to an external operation to the display image and output the overlapped image to the display device; and a control unit configured to perform a predetermined process on at least one select region which is selected according to the external operation.

Moreover, the above-described endoscope system according to the present invention further includes an operating unit configured to output a select signal to select any one of the plurality of select regions, wherein the display controller is configured to highlight the select region which is selected according to the select signal output from the operating unit.

Moreover, in the above-described endoscope system according to the present invention, the display controller is configured to transition the select region to another select region and highlight the select region whenever the operating unit outputs the select signal.

Moreover, in the above-described endoscope system according to the present invention, the operating unit is provided rotatably about an axis perpendicular to a light-receiving surface of the imaging unit, and is configured to output the select signal at each predetermined rotation angle.

Moreover, the above-described endoscope system according to the present invention further includes a camera head to which the endoscope is detachably connected, wherein the camera head includes the imaging unit, and wherein number of effective pixels of the imaging unit is 8 mega-pixels or more.

Moreover, in the above-described endoscope system according to the present invention, the endoscope includes an insertion unit configured to be inserted to the subject, the imaging unit is provided in a distal end portion of the insertion unit, and number of effective pixels of the imaging unit is 2 mega-pixels or more.

Moreover, in the above-described endoscope system according to the present invention, a monitor size of the display device is 31 inches or more.

Moreover, a processing method according to the present invention includes: processing an image signal generated by an imaging unit to generate a display image to be displayed; overlapping a plurality of select regions selectable according to an external operation to the display image to output the overlapped image to a display device; and performing a predetermined process on at least one select region which is selected according to an external operation.

Moreover, a program according to the present invention causes a control device to execute: processing an image signal generated by an imaging unit to generate a display image to be displayed; overlapping a plurality of select regions selectable according to an external operation to the display image to output the overlapped image to a display device; and performing a predetermined process on at least one select region which is selected according to an external operation.

Advantageous Effects of Invention

According to the invention, even a region other than the center region in an image can be selected and be subjected to a predetermined process.

BEST MODE FOR CARRYING OUT THE INVENTION

Figure 1:
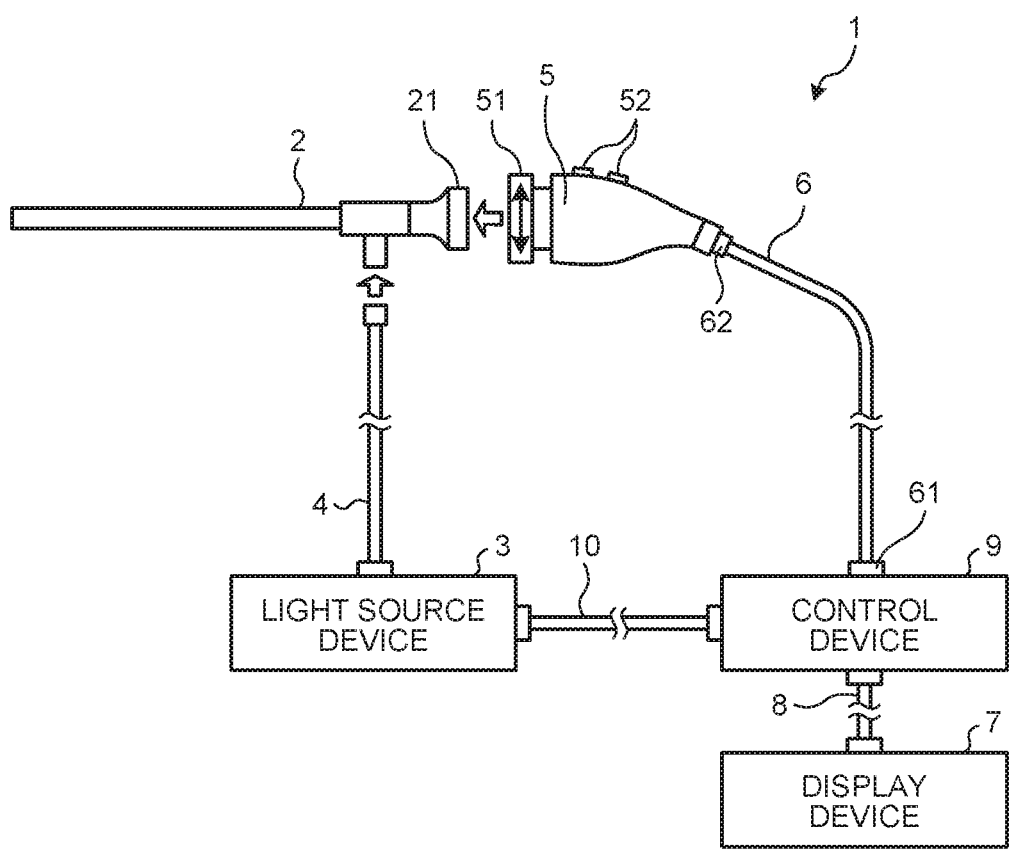
FIG. 1 is a diagram illustrating a schematic configuration of an endoscope system according to a first embodiment of the invention.

Hereinafter, modes for carrying out the invention will be described in detail using the drawings. Further, the invention is not limited to the following embodiments. In addition, the drawings referred in the following description schematically illustrate shapes, sizes, and positional relations to an extent for helping with understanding on the contents of the invention. In other words, the invention is not limited to the shapes, the sizes, and the positional relations illustrated in the drawings. Further, the same portions in the drawings will be attached with the same symbol.

First Embodiment

[Schematic Configuration of Endoscope System]

FIG. 1 is a diagram illustrating a schematic configuration of an endoscope system according to a first embodiment of the invention.

An endoscope system 1 illustrated in FIG. 1 is a device which is used in medical fields to capture an image of a subject such as an organ. Further, in the first embodiment, the description of the endoscope system 1 will be given about a rigid endoscope system which uses a rigid endoscope (an insertion unit 2) illustrated in FIG. 1. However, the invention is not limited to the above configuration, and a flexible endoscope system may be applied.

As illustrated in FIG. 1, the endoscope system 1 includes the insertion unit 2 (endoscope), a light source device 3, a light guide 4, a camera head 5 (an image capturing device for an endoscope), a first transmission cable 6, a display device 7, a second transmission cable 8, a control device 9, and a third transmission cable 10.

The insertion unit 2 is rigid or at least partially flexible and formed in an elongated shape, and is inserted into a subject such as a body of a patient. The inside of the insertion unit 2 is configured using one or a plurality of lenses, and an optical system is provided to form an observation image.

The light source device 3 is connected to one end of the light guide 4, and emits (supplies) an illumination light to illuminate the inside of the subject to the one end of the light guide 4 according to the control of the control device 9. The light source device 3 is configured using a solid light-emitting element such as an LED (Light Emitting Diode) and an LD (Laser Diode), a discharge lamp such as a xenon lamp and a metal halide lamp, and a light-emitting member such as a halogen lamp.

The one end of the light guide 4 is detachably connected to the light source device 3, and the other end is detachably connected to the insertion unit 2. The light guide 4 transfers the light output from the light source device 3 to the other end from the one end, and supplies the light to the insertion unit 2.

The camera head 5 is detachably connected to an eyepiece 21 of the insertion unit 2. The camera head 5 captures an observation image formed by the insertion unit 2 according to the control of the control device 9, converts the image signal (electric signal) into an optical signal, and outputs the optical signal. In addition, the camera head 5 includes an operation ring 51 which is provided rotatably in a circumferential direction, and a plurality of input units 52 which receive command signals giving an instruction on various types of operations of the endoscope system 1. Further, the detailed configuration of the camera head 5 will be described below.

One end of the first transmission cable 6 is detachably connected to the control device 9 through a first connector 61, and the other end is connected to the camera head 5 through a second connector 62. The first transmission cable 6 transfers an image capture signal output from the camera head 5 toward the control device 9, and transfers a control signal, a synchronization signal, a clock, and power output from the control device 9 to the camera head 5.

The display device 7 displays a display image and various types of information related to the endoscope system 1 based on the image signal processed in the control device 9 according to the control of the control device 9. In addition, a monitor size of the display device 7 is 31 inches or more, preferably 55 inches or more. Further, in the first embodiment, the display device 7 is configured to have a monitor size of 31 inches or more, but the invention is not limited thereto. Other monitor sizes (for example, a monitor size which can display an image of a resolution of 8 mega-pixels (so-called 4K resolution of 3840×2160 pixels) or more may be used.

One end of the second transmission cable 8 is detachably connected to the display device 7, and the other end is detachably connected to the control device 9. The second transmission cable 8 transfers a video signal processed in the control device 9 to the display device 7.

The control device 9 is configured by a CPU (Central Processing Unit), a GPU (Graphics Processing Unit), and various types of memories. The control device 9 collectively controls the operations of the light source device 3, the camera head 5, and the display device 7 through each of the first transmission cable 6, the second transmission cable 8, and the third transmission cable 10 according to a program recorded in a memory (not illustrated). Further, the detailed configuration of the control device 9 will be described below.

One end of the third transmission cable 10 is detachably connected to the light source device 3, and the other end is detachably connected to the control device 9. The third transmission cable 10 transfers the control signal from the control device 9 to the light source device 3.

Figure 2:
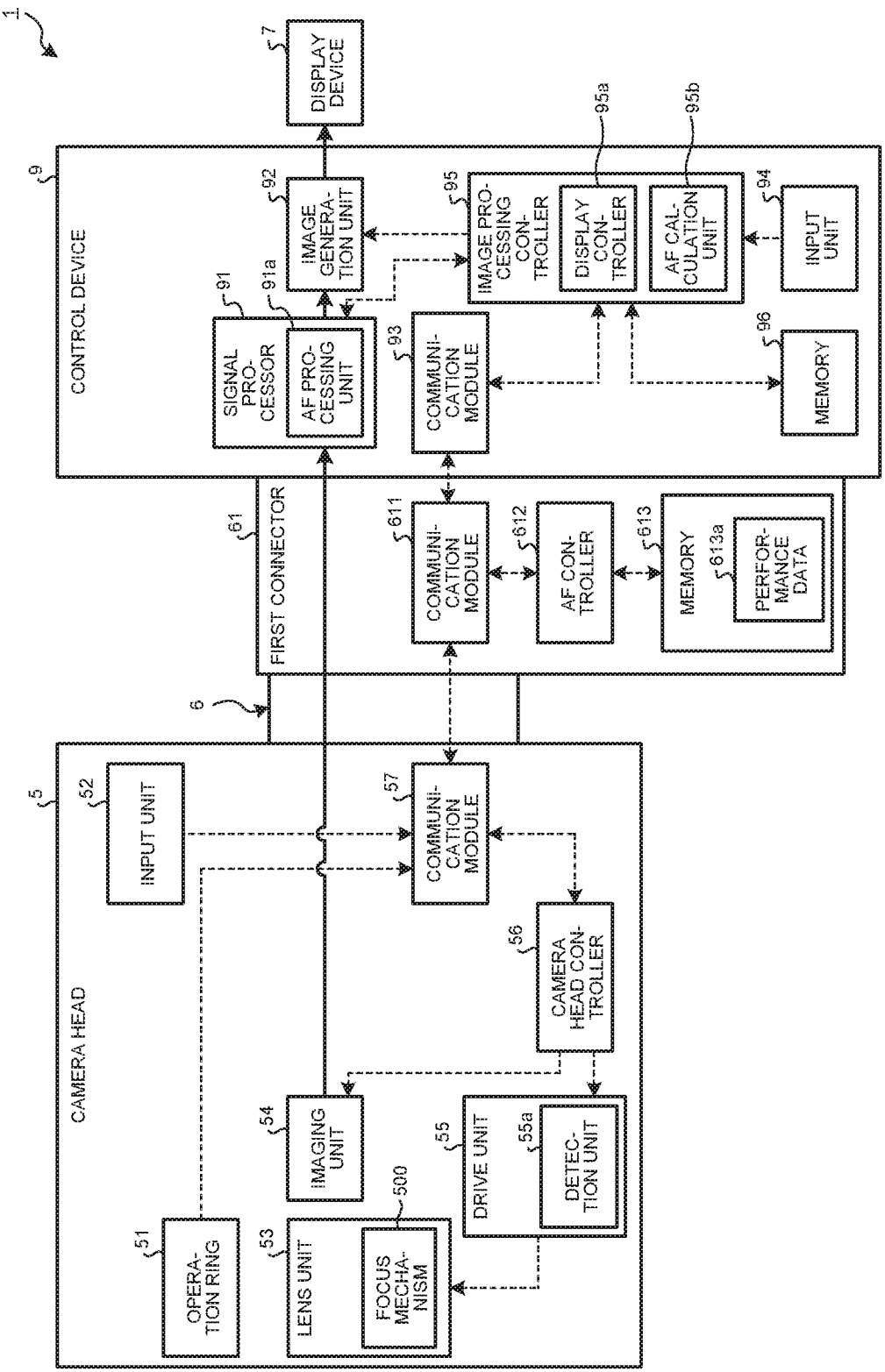
FIG. 2 is a block diagram illustrating a functional configuration of a camera head, a first connector, and a control device which are included in the endoscope system according to the first embodiment of the invention.

Next, the functional configurations of the camera head 5, the first connector 61 of the first transmission cable 6, and the control device 9 will be described. FIG. 2 is a block diagram illustrating the functional configurations of the camera head 5, the first connector 61, and the control device 9 of the endoscope system 1. Further, in FIG. 2, the second connector 62 between the camera head 5 and the control device 9 and the first transmission cable 6 will be omitted for the convenience of description.

[Configuration of Camera Head]

First, the configuration of the camera head 5 will be described.

The camera head 5 includes the operation ring 51, the input unit 52, a lens unit 53, an imaging unit 54, a drive unit 55, a camera head controller 56, and a communication module 57 as illustrated in FIG. 2.

The operation ring 51 is provided rotatably in the circumferential direction, and outputs a select signal to select various types of operations of the endoscope system 1 by rotating along with a user's rotation operation. Specifically, the operation ring 51 is rotatably provided about an axis perpendicular to a light-receiving surface of the imaging unit 54, and outputs the select signal at every predetermined rotation angle. The operation ring 51 is configured by, for example, a PI/PR method where an operation ring, a photo interrupter (not illustrated), a photo reflector (not illustrated), and a comb-tooth member (not illustrated) are used. A pulse-like select signal corresponding to a comb-tooth is output by a photo interrupter according to the rotation of the operation ring. Further, the operation ring 51 may be provided movably back and forth with respect to the insertion direction of the insertion unit 2 other than the circumferential direction. In addition, besides the PI/PR method, the operation ring 51 may be configured in a variable resistance manner using a magnetic or a hole element.

A plurality of the input units 52 are provided in the upper end of the camera head 5, and receive the command signals giving an instruction on various types of operations of the endoscope system 1. The input unit 52 is configured using a button and a switch.

The lens unit 53 is configured using one or a plurality of lenses, and forms a subject image focused by the insertion unit 2 in an imaging face of an image sensor (not illustrated) which forms the imaging unit 54. One or the plurality of lenses are configured to be movable along the optical axis. Then, a focus mechanism 500 is provided in the lens unit 53 to move one or the plurality of lenses and change the position of at least the focus. In addition to the focus mechanism 500, the lens unit 53 may be provided with a zoom mechanism, an aperture mechanism, and an optical filter (for example, a filter for cutting an infrared light) which can be mounted or demounted onto the optical axis.

Figure 3:
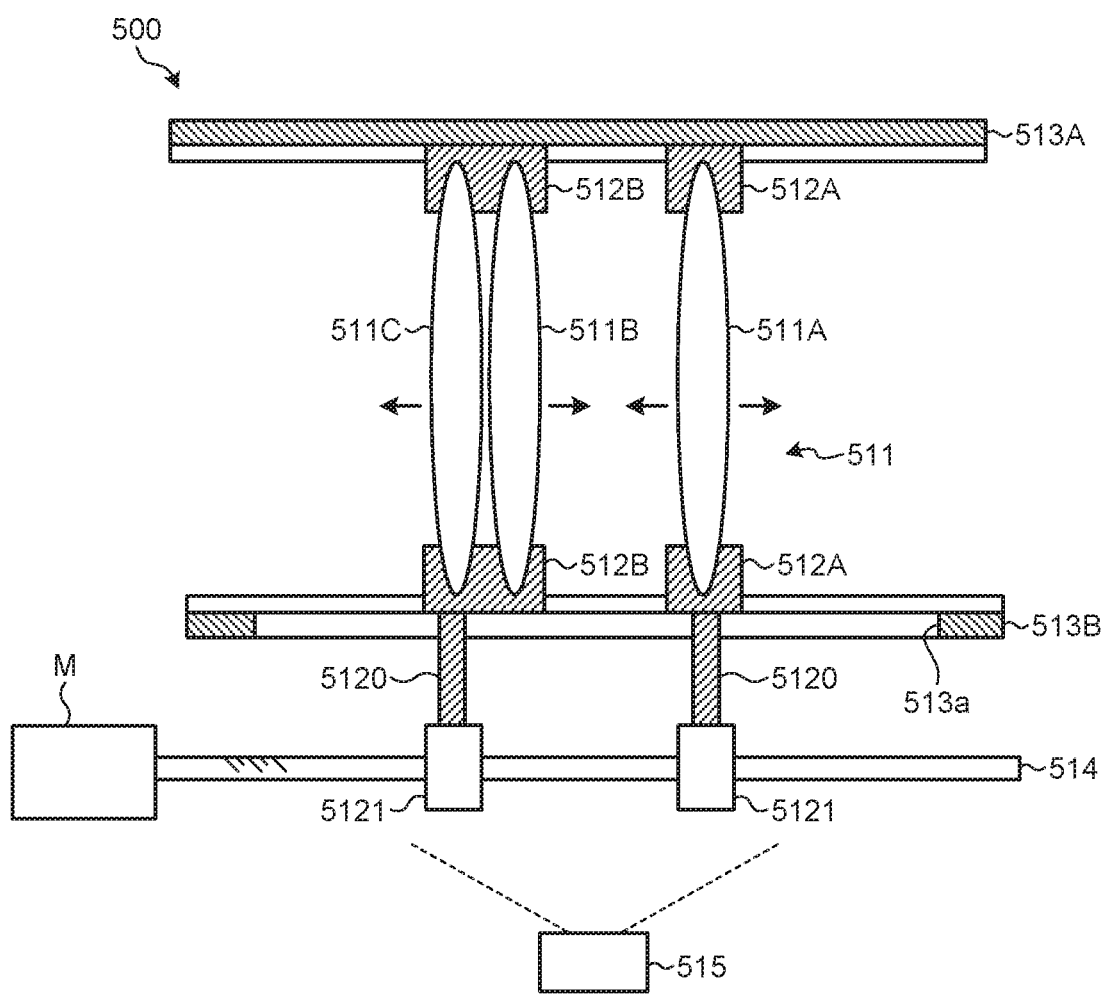
FIG. 3 is a schematic diagram for describing a focus mechanism of a lens unit illustrated in FIG. 2.

Herein, the focus mechanism 500 of the lens unit 53 will be described with reference to FIG. 3. FIG. 3 is a schematic diagram for describing the focus mechanism 500 of the lens unit 53 illustrated in FIG. 2.

The focus mechanism 500 illustrated in FIG. 3 includes a lens group 511 of a plurality of lenses (lenses 511A to 511C), a first lens frame 512A, a second lens frame 512B, a first support shaft 513A, a second support shaft 513B, a rotation shaft 514, a motor M, and a lens position detector 515.

The lens group 511 is held by the lens frame (the first lens frame 512A and the second lens frame 512B: movable optical member), and is provided to be movable along the axial direction of the rotation shaft 514. In the first embodiment, the lens 511A to 511C will be described to move in the optical axis direction by the first lens frame 512A holding the lens 511A, and the second lens frame 512B holding the lenses 511B and 511C. Further, the lenses in the focus mechanism 500 may be configured by three lenses as illustrated in FIG. 3, or may be configured one lens, or two or four or more lenses.

The first lens frame 512A holds the lens 511A. In addition, the first lens frame 512A is provided with a transmission mechanism which is screwed with the rotation shaft 514 and includes a first transmission unit 5120 to convert a rotation power of the rotation shaft 514 into a propulsion force of the optical axis direction and a second transmission unit 5121 to transfer the propulsion force converted by the first transmission unit 5120 to the first lens frame 512A. Further, the lens frame holds the lens, and is not limited to this configuration as long as the movement in the optical axis direction can be made.

The second lens frame 512B holds the lens 511B and 511C. In addition, the second lens frame 512B is provided with a transmission mechanism which is screwed with the rotation shaft 514 and includes the first transmission unit 5120 to convert the rotation power of the rotation shaft 514 into the propulsion force of the optical axis direction and the second transmission unit 5121 to transfer the propulsion force converted by the first transmission unit 5120 to the second lens frame 512B.

The first support shaft 513A and the second support shaft 513B extend in the optical axis direction, hold the first lens frame 512A and the second lens frame 512B not to make each lens of the lens group 511 inclined with respect to the optical axis, and hold each lens (lens frame) of the lens group 511 to be movable in the optical axis direction. In the second support shaft 513B, a through hole 513a is formed for the second transmission unit 5121 to be inserted.

The rotation shaft 514 is connected to the motor M, and rotates about the longitudinal shaft according to the rotation power from the motor M. In the rotation shaft 514, a helicoidal groove is formed. The first transmission unit 5120 is engaged with the groove, and converts the rotation of the rotation shaft 514 into the propulsion force to the axial direction.

In this way, in the focus mechanism 500, the motor M rotates according to the control of the drive unit 55, so that the rotation shaft 514 rotates. With the rotation of the rotation shaft 514, the first lens frame 512A and the second lens frame 512B move along the axial direction through the first transmission unit 5120 and the second transmission unit 5121. With this configuration, it is possible to move the lenses 511A to 511C which are held in the respective lens frames in the axial direction.

The lens position detector 515 detects distances from reference positions of the first lens frame 512A and the second lens frame 512B, The lens position detector 515 emits an infrared light for example, and receives a reflected light from the lens to output a detection signal (optical detection signal) indicating at which positions (distances) the first lens frame 512A and the second lens frame 512B are located with respect to the reference positions to a detection unit 55a. The lens position detector 515 may use a photo interrupter instead of measuring the distance using the infrared light.

Returning to FIG. 2, the description of the configuration of the camera head 5 will be continued.

The imaging unit 54 captures an image of the subject according to the control of the camera head controller 56. The imaging unit 54 is configured using a sensor chip in which an image sensor (not illustrated) such as a CCD (Charge Coupled Device) or a CMOS (Complementary Metal Oxide Semiconductor) which generates an image signal (electric signal) by performing a photoelectric conversion on the received subject image formed by the insertion unit 2 and the lens unit 53 is integrated. In the case of the CCD, for example, a signal processor (not illustrated) which performs a signal processing (A/D conversion) on the image signal (analog signal) from the image sensor and outputs the image capture signal is mounted in a sensor chip. In the case of the CMOS, for example, a signal processor which performs the signal processing (A/D conversion) on the image signal (analog signal) converted from the light to the electric signal and outputs the image capture signal is included in the image sensor. In addition, the number of effective pixels of the imaging unit 54 (image sensor) is 8 mega-pixels or more (for example, a so-called 4K resolution of 3840×2160 pixels). In this case, as the number of effective pixels of the imaging unit 54 is increased, the depth of the subject is narrowed, and the focusing of the lens unit 53 becomes hard except the center region. However, with the process described below, even the region other than the center region can be focused with the lens unit 53. Further, in the first embodiment, the imaging unit 54 will be described to output, for example, RAW data with the optical signal.

The drive unit 55 includes a driver (not illustrated) which operates the motor M of the focus mechanism 500 according to the control of the camera head controller 56, and changes the focusing position of the lens unit 53. In addition, the drive unit 55 includes the detection unit 55a which receives the detection signal of the position (reference position) of the lens in the lens unit 53, and outputs the signal to the camera head controller 56.

The camera head controller 56 controls the operation of the entire camera head 5 according to a drive signal input from the first connector 61 through the first transmission cable 6, the select signal from the operation ring 51, and the command signal from the input unit 52. The camera head controller 56 outputs information related to the current state of the camera head 5 to the control device 9 through the first transmission cable 6. The camera head controller 56 is realized by a general processor such as a CPU which includes an inner memory (not illustrated) with a program recorded and a dedicated processor such as various types of arithmetic circuits which perform specific functions such as an ASIC (Application Specific Integrated Circuit). In addition, there may be configured using an FPGA (Field Programmable Gate Array: not illustrated) which is a type of programmable integrated circuits. Further, in a case where the FPGA is used, a memory is provided to store configuration data. The FPGA (programmable integrated circuit) may be configured with the configuration data read out of the memory.

The communication module 57 outputs a signal transmitted from the first transmission cable 6 including an AF drive signal (described below) and a signal transmitted from the control device 9 to each unit in the camera head 5. In addition, the communication module 57 converts the information related to the current state of the camera head 5 into a signal format according to a predetermined transmission scheme, and outputs the converted signal to the first connector 61 and the control device 9 through the first transmission cable 6.

[Configuration of First Connector]

Next, the configuration of the first connector 61 of the first transmission cable 6 will be described.

As illustrated in FIG. 2, the first connector 61 includes a communication module 611, an AF controller 612, and a memory 613.

The communication module 611 outputs a signal transmitted from the control device 9 such as a control signal containing a result of an AF calculating process (described below) and a signal transmitted from the camera head 5 to the AF controller 612. In addition, the communication module 611 outputs a signal transmitted from the AF controller 612 containing the AF drive signal (described below) to the camera head 5 and the control device 9.

The AF controller 612 controls a focus drive of the drive unit 55 of the camera head 5. The AF controller 612 generates the AF drive signal with reference to performance data (for example, a read timing and a lens drive) 613a for the AF control which is recorded in the memory 613 according to the result of the AF calculating process from an AF calculation unit 95b of the control device 9 (described below) through the communication module 611, and transmits the generated AF drive signal to the camera head 5 through the communication module 611 and the first transmission cable 6. The AF controller 612 is realized using an ASIC or an FPGA.

The memory 613 is realized using a semiconductor memory such as a flash memory or a DRAM (Dynamic Random Access Memory), and stores various types of programs performed by the AF controller 612. In addition, the memory 613 stores the performance data 613a related to the AF performance of the camera head 5 as unique information. The performance data 613a includes, for example, performance data related to the AF drive such as information of a moving distance (a distance between frames) of lenses between frames captured in the AF process, setting information of a driver of the drive unit 55 of the camera head 5, information of a lens moving amount with respect to an input signal of the focus mechanism 500, and individual deviation data of the drive unit 55 including a detection unit 55a and the lens unit 53 including the focus mechanism 500.

In addition, in the first embodiment, the AF controller 612 and the memory 613 are provided in the first connector 61, but the invention is not limited thereto. At least one may be provided in the second connector 62, in another portion of the first transmission cable 6, or the control device 9 (described below). Of course, the AF controller 612 may be provided in the camera head 5.

[Configuration of Control Device]

Next, the configuration of the control device 9 will be described.

The control device 9 includes, as illustrated in FIG. 2, a signal processor 91, an image generation unit 92, a communication module 93, an input unit 94, an image processing controller 95, and a memory 96. Further, in the control device 9, there may be provided a power source unit (not illustrated) which generates a power source voltage to drive the control device 9 and the camera head 5, supplies the voltage to each unit of the control device 9, and supplies the voltage to the camera head 5 through the first transmission cable 6.

The signal processor 91 performs the O/E conversion on the image signal of the optical signal output from the camera head 5, performs a noise removal on the converted image signal and the signal processing such as the A/D conversion as needed, and outputs the digitized image signal to the image generation unit 92. In addition, the signal processor 91 includes an AF processing unit 91a.

The AF processing unit 91a calculates a predetermined AF evaluation value of each frame based on the image signal of the input frame, and outputs the calculated AF evaluation value to the image processing controller 95. Further, the AF processing unit 91a calculates the AF evaluation value of each select region based on the image signal of each of a plurality of select regions overlapped with the display image (described below) selected by the operation ring 51, and outputs the calculated AF evaluation value of each select region to the image processing controller 95. Further, the AF processing unit 91a may calculate the AF evaluation value of only the select region which is selected by the operation ring 51. Of course, the AF processing unit 91a may calculate the AF evaluation value of a combined region (zone region) obtained by combining two or more select regions among the plurality of select regions selected by the operation ring 51 or the input unit 52.

The image generation unit 92 generates the display image (video signal) for display displayed by the display device 7 based on the image signal input from the signal processor 91. Specifically, the image generation unit 92 performs a predetermined signal processing on the image signal to generate a display signal (video signal) to be displayed including the subject image. Herein, examples of the image processing include various types of image processing such as color compensation, color enhancement, contour enhancement, and masking process. The image generation unit 92 outputs the generated display image (video signal) to the display device 7. The image generation unit 92 is configured using a CPU, an ASIC, or an FPGA.

The communication module 93 outputs a signal from the control device 9 which contains the control signal (described below) transmitted from the image processing controller 95 to the camera head 5. In addition, the signal from the camera head 5 is output to the control device 9.

The input unit 94 is realized using user interfaces such as a keyboard, a mouse, and a touch panel, and receives various types of information. In addition, the input unit 94 may be provided rotatably about a predetermined shaft, and realized using a jog dial to output the select signal to every predetermined rotation angle. Of course, the input unit 94 may be configured using a button and a switch, and output the select signal and the command signal whenever being pressed.

The image processing controller 95 performs drive control of each component including the control device 9 and the camera head 5, and input/output control of information with respect to each component. The image processing controller 95 generates the control signal containing a result of the AF calculating process (described below) with reference to communication information data (for example, communication format information) recorded in the memory 96, and transmits the generated control signal to the first connector 61 through the communication module 93. In addition, the image processing controller 95 outputs the control signal to the camera head 5 through the first transmission cable 6. In addition, the image processing controller 95 generates the synchronization signal of the imaging unit 54 and the control device 9, and a clock. The synchronization signal to the camera head 5 (for example, a synchronization signal indicating an image capture timing of the camera head 5) and a clock (for example, a clock for a serial communication) are sent to the camera head 5 through a line (not illustrated), and drives the camera head 5 based on the synchronization signal and the clock. The image processing controller 95 is realized using a CPU, an ASIC, or an FPGA. The image processing controller 95 includes a display controller 95a, and the AF calculation unit 95b.

The display controller 95a overlaps the plurality of select regions to the display image subjected to the image processing of the image generation unit 92 according to the operation of the operation ring 51, the input unit 52, or the input unit 94, and outputs the overlapped image to the display device 7. In addition, the display controller 95a highlights the select region thus selected according to the select signal output by the operation ring 51. Further, the display controller 95a transitions the select region to another select region whenever the select signal is input from the operation ring 51, and highlights the select region.

The AF calculation unit 95b performs the AF calculating process to select a focus lens position most appropriate as a focus position from the AF evaluation value of each frame from the AF processing unit 91a or the AF evaluation value of the select region selected by the operation ring 51 or the input unit 52. Specifically, in a case where any one of the plurality of select region is selected by the operation ring 51 or the input unit 52, the AF calculation unit 95b performs the AF calculating process to make the lens unit 53 focused on the select region thus selected. Then, the AF calculation unit 95b outputs the calculation result to the AF controller 612 of the first connector 61 through the communication module 93.

The memory 96 is realized using a semiconductor memory such as a flash memory or a DRAM, and records communication information data (for example, communication format information). Further, the memory 96 records various types of programs performed by the image processing controller 95 or the endoscope system 1.

Further, in the first embodiment, the AF processing unit 91a is provided in the signal processor 91, and the AF calculation unit 95b is provided in the image processing controller 95, but the invention is not limited thereto. The AF processing unit 91a and the AF calculation unit 95b may be provided collectively in any one of the signal processor 91 and the image processing controller 95, or may be provided in separate devices. Of course, the AF processing unit 91a and the AF calculation unit 95b may be provided in the camera head 5 or the first connector 61.

[Outline of AF Processing of Endoscope System]

Next, the AF processing of the endoscope system 1 will be described.

In a case where the image signals of a plurality of frames (at least two or more frames) sequentially generated by the imaging unit 54 while the focus lens is moved on the optical axis by the focus mechanism 500 are input, the AF processing unit 91a outputs the AF evaluation value for each frame. At this time, the AF processing unit 91a calculates the AF evaluation value with respect to the center region of each frame (each display image). In addition, in a case where any one of the plurality of select regions overlapped on the display image is selected by the operation ring 51 or the input unit 52, the AF processing unit 91a calculates the AF evaluation value of the select region which is selected for each frame.

Thereafter, the AF calculation unit 95b selects a frame most appropriate as the focus position of the lens unit 53 based on the AF evaluation value, and generates optimal frame information (focus evaluation) which is information of a frame optimal to the focus. Then, the AF calculation unit 95b outputs an AF control signal containing the optimal frame information to the AF controller 612 through the communication modules 93 and 611. The AF control signal may contain information of a moving direction of the lens of the lens unit 53 (a direction away from or closer to the subject).

Subsequently, in a case where the AF control signal is received, the AF controller 612 generates the AF drive signal to move the lens group 511 (the first lens frame 512A and the second lens frame 512B) to a moving direction up to the position corresponding to the optimal frame information and a moving distance (for example, a moving distance from the current position up to a position corresponding to the optimal frame information) with reference to the performance data 613a, and outputs the generated AF drive signal to the camera head controller 56 through the communication modules 611 and 57. The camera head controller 56 controls the drive unit 55 based on the received AF drive signal, and moves the lens group 511 (the first lens frame 512A and the second lens frame 512B). At this time, the drive unit 55 rotates the rotation shaft 514 according to the optimal frame information from the current position while checking the detection result of the detection unit 55a, and moves the lens group 511 (the first lens frame 512A and the second lens frame 512B). With this configuration, the AF controller 612 can make the lens unit 53 be focused on the center region or the select region.

Further, the selection of a frame using the AF calculation unit 95b may be realized using a well-known AF scheme such as a contrast AF or an AF using a space recognition technique. The AF processing unit 91a outputs a well-known AF evaluation value according to an AF scheme to be employed such as a contrast value of each frame. The AF calculation unit 95b selects a frame based on the well-known AF evaluation value according to an AF scheme to be employed such as a frame of which the contrast value is largest.

[Process of Endoscope System]

Next, a process performed by the endoscope system 1 will be described.

Figure 4:
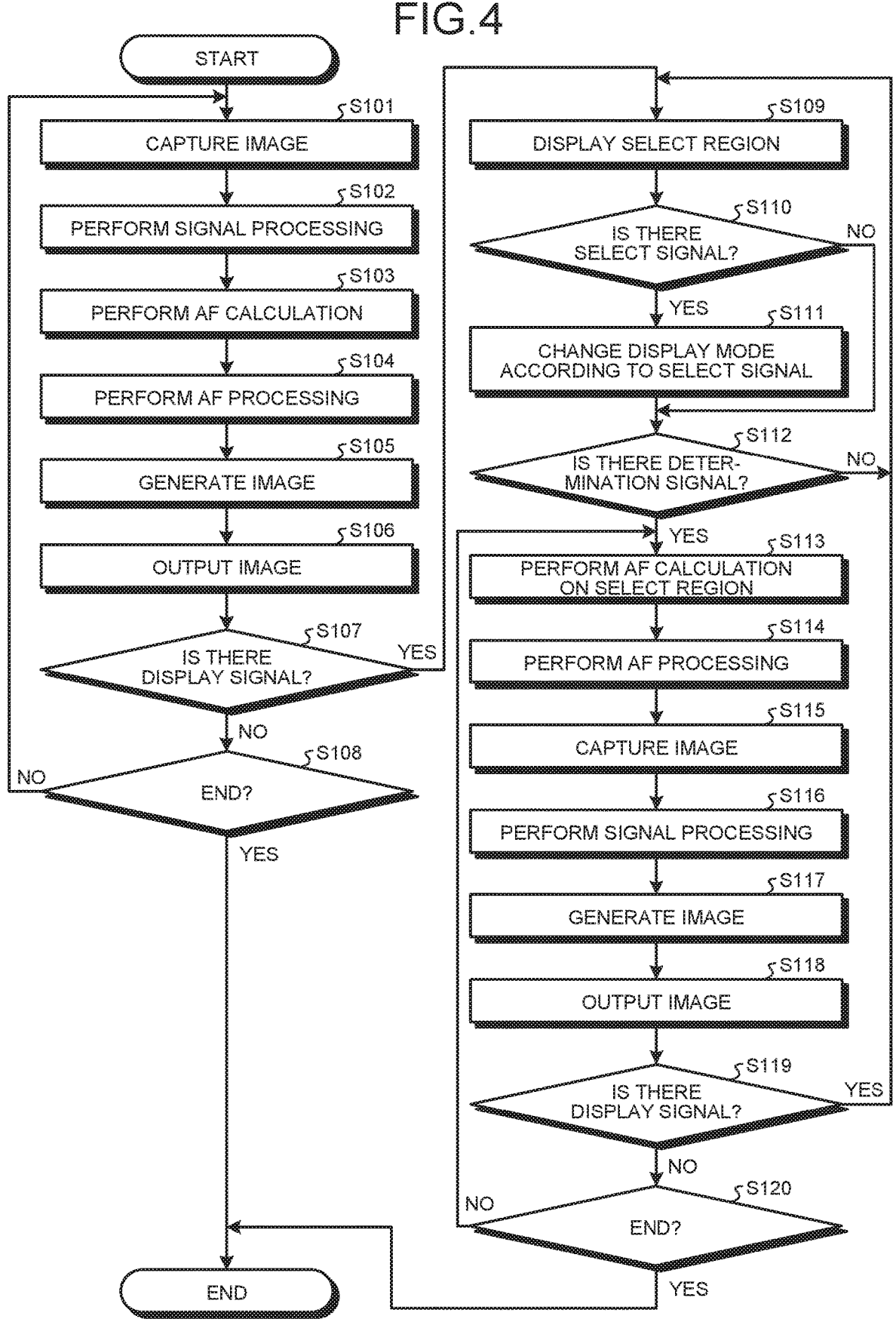
FIG. 4 is a flowchart illustrating the outline of a process performed by the endoscope system according to the first embodiment of the invention.

FIG. 4 is a flowchart illustrating the outline of a process performed by the endoscope system 1.

As illustrated in FIG. 4, first, the imaging unit 54 sequentially captures images of the subject which are formed by the insertion unit 2 and the lens unit 53 (Step S101).

Subsequently, the signal processor 91 performs the signal processing on the image signal sequentially input through the first transmission cable 6 (Step S102).

Thereafter, the AF processing unit 91a and the AF calculation unit 95b performs the AF calculation on the image signal sequentially subjected to the signal processing by the signal processor 91 to calculate an AF focus value (Step S103). In this case, the AF processing unit 91a calculates the AF focus value with respect to the center region of the display image corresponding to the image signal. Further, the AF calculation unit 95b selects a frame most appropriate as the focus position of the lens unit 53 based on the AF evaluation value calculated by the AF processing unit 91a, and generates the optimal frame information (focus evaluation) which is information of the frame optimal to the focus. Then, the AF calculation unit 95b outputs an AF control signal containing the optimal frame information to the AF controller 612 through the communication modules 93 and 611.

Subsequently, the AF controller 612 controls the focus drive using the drive unit 55 of the camera head 5 to perform the AF process (Step S104).

Figure 5:
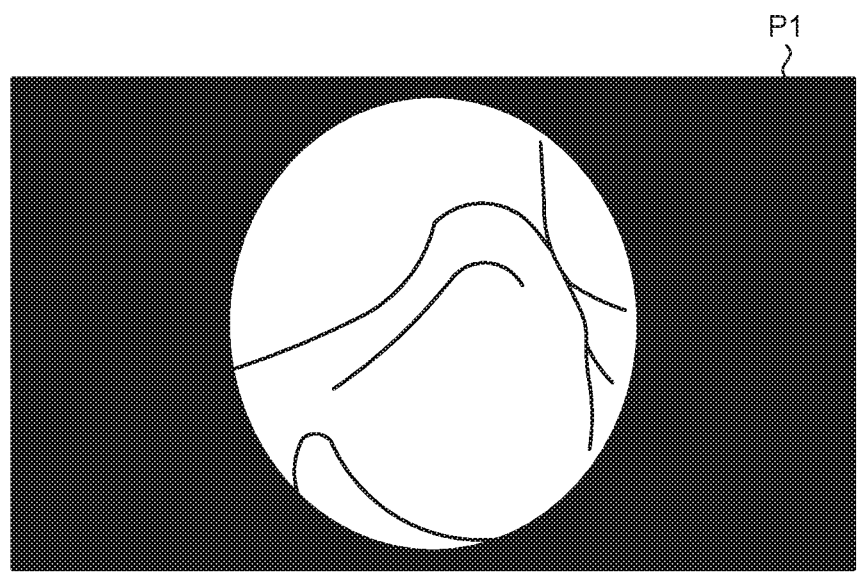
FIG. 5 is a diagram schematically illustrating an example of a display image displayed by a display device according to the first embodiment of the invention.

Thereafter, the image generation unit 92 generates the display image to be displayed in the display device 7 based on the image signal sequentially subjected to the signal processing by the signal processor 91 (Step S105), and outputs the display image to the display device 7 (Step S106). With this configuration, as illustrated in FIG. 5, the display device 7 can display a display image P1 which is focused at the center region.

Subsequently, in a case where the display signal to display the select region on the display image P1 displayed by the display device 7 is input from the operation ring 51 or the input unit 52 (Step S107: Yes), the endoscope system 1 proceeds to Step S109 described below. With this regard, in a case where the display signal to display the select region on the display image P1 displayed by the display device 7 is not input from the operation ring 51 or the input unit 52 (Step S107: No), the endoscope system 1 proceeds to Step S108 described below.

In Step S108, in a case where an end signal to end the observation on the subject is input from the input unit 94 (Step S108: Yes), the endoscope system 1 ends this process. With this regard, in a case where the end signal to end the observation on the subject is not input from the input unit 94 (Step S108: No), the endoscope system 1 returns to Step S101.

Figure 6:
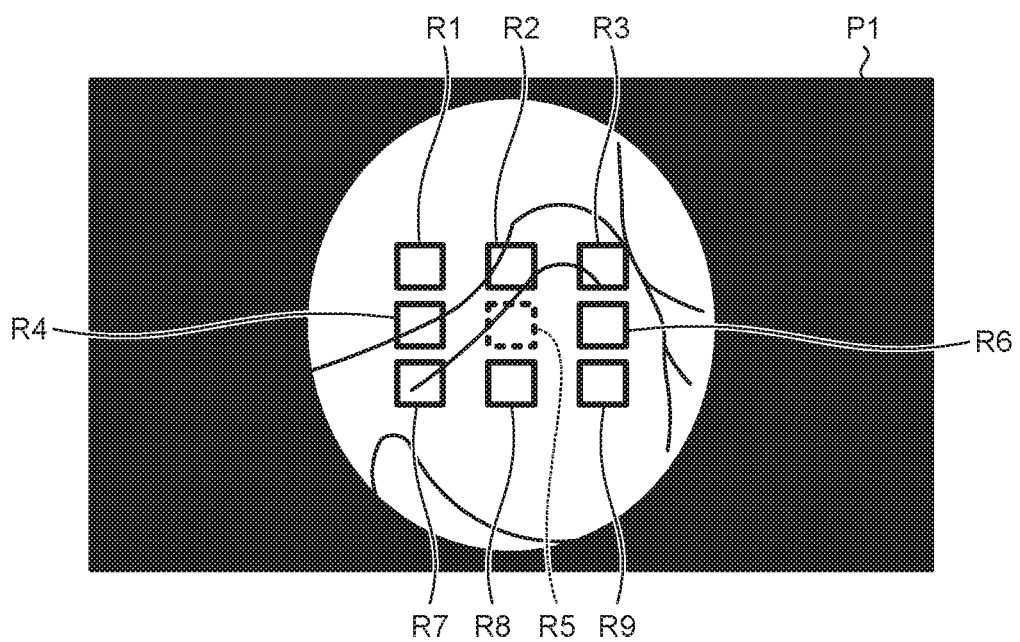
FIG. 6 is a diagram schematically illustrating an example of a plurality of select regions overlapped in the display image displayed by the display device according to the first embodiment of the invention.

In Step S109, the display controller 95a causes the display device 7 to display the plurality of select regions to be overlapped on the display image P1 displayed by the display device 7. Specifically, as illustrated in FIG. 6, the display controller 95a causes the display device 7 to display a plurality of select regions R1 to R9 to be overlapped on the display image P1. In this case, the display controller 95a highlights the select region R5 at the center corresponding to the position of the current focus among the plurality of select regions R1 to R9 (illustrated with a broken line in FIG. 6). At this time, the display controller 95a may change a display mode of the select region R5 according to the focus state of the lens unit 53. For example, in a case where the lens unit 53 is focused on the select region R5, the display controller 95a highlights the contour of the select region R5 with red. In a case where the lens unit 53 is not focused on the select region R5, the contour of the select region R5 is blinked with yellow. With this configuration, the user can intuitively grasp the focus position and the focus state of the current lens unit 53. Further, the control device 9 may make an output unit (not illustrated) such as a speaker output a voice indicating the fact that the lens unit is in focus.

Figure 7:
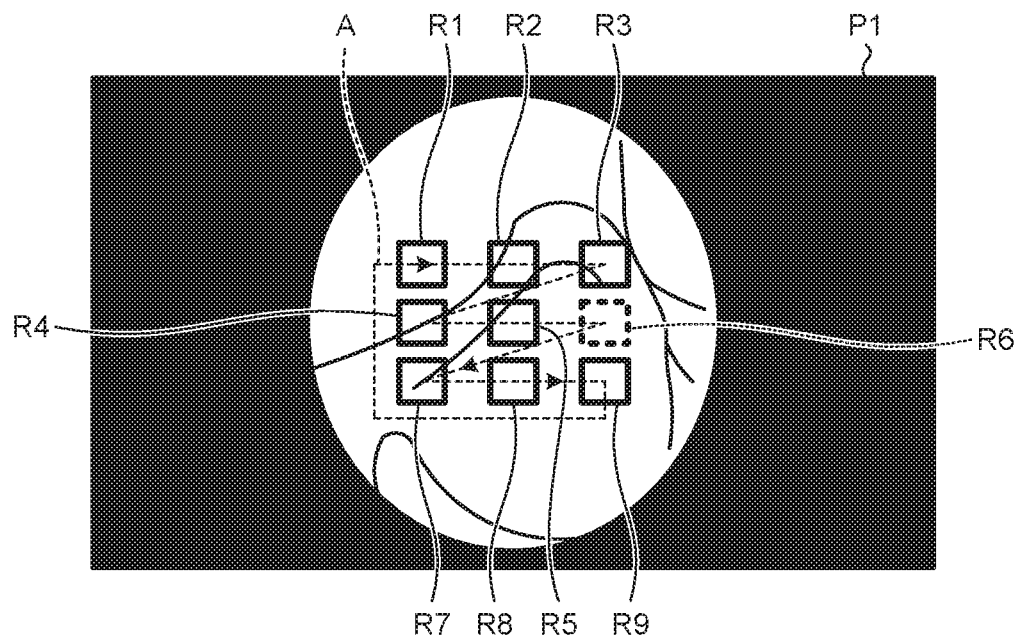
FIG. 7 is a diagram schematically illustrating an example of transitions of the plurality of select regions overlapped in the display image displayed by the display device according to the first embodiment of the invention.

Subsequently, the user performs the rotation operation on the operation ring 51. In a case where the select signal to select any one of the plurality of select regions is input from the operation ring 51 (Step S110: Yes), the display controller 95a changes the display modes of the plurality of select regions R1 to R9 according to the select signal input from the operation ring 51 (Step S111). Specifically, the display controller 95a changes the select region to make highlighting according to the number of pulses of the select signal input from the operation ring 51. For example, as illustrated with arrow A of FIG. 7, the display controller 95a sequentially highlights the select regions R6, R7, R8, R9, R1, R2, R3, R4, and R5 from the select region R5 at the center according to the number of pulses of the select signal input from the operation ring 51. With this configuration, the user can make selection while intuitively grasping a desired select region among the plurality of select regions R1 to R9. Further, the display controller 95a may highlight the select regions in reverse order according to the rotation direction of the operation ring 51. In addition, the display controller 95a changes the highlighting position of the select region according to the number of pulses of the select signal from the operation ring 51. For example, the highlighting position may be changed according to the number of times of operation (the number of times of pressing) of the input unit 52. Further, the display controller 95a may change the display sizes of the plurality of select regions R1 to R9 according to the number of times of operations (the number of times of pressing) of the input unit 52. For example, the display controller 95a may change the display mode such that the display sizes of the plurality of select regions R1 to R9 are increased whenever the input unit 52 is pressed. Of course, the display controller 95a may change the display mode such that the display sizes of the plurality of select regions R1 to R9 are decreased whenever the input unit 52 is pressed. Further, the display controller 95a may change the display sizes or the number of the plurality of select regions R1 to R9 according to the number of times that the operation ring 51 moves back and forth.

Thereafter, in a case where a determination signal to determine any one of the plurality of select regions is input from the input unit 52 (Step S112: Yes), the AF processing unit 91a and the AF calculation unit 95b perform the AF calculation on the select region selected according to the determination signal to calculate the AF focus value (Step S113). In this case, in the display image P1 displayed by the display device 7, the AF focus value is calculated with respect to the select region selected according to the determination signal. Further, the AF calculation unit 95b selects a frame most appropriate as the focus position of the lens unit 53 based on the AF evaluation value calculated by the AF processing unit 91a, and generates the optimal frame information (focus evaluation) which is information of a frame optimal to the focus. Then, the AF calculation unit 95b outputs an AF control signal containing the optimal frame information to the AF controller 612 through the communication modules 93 and 611.

Subsequently, the AF controller 612 controls the focus drive using the drive unit 55 of the camera head 5 to perform the AF process in which the lens unit 53 is focused on the select region selected by the user (Step S114).

Thereafter, the imaging unit 54 captures the subject image formed by the insertion unit 2 and the lens unit 53 (Step S115).

Subsequently, the signal processor 91 performs the signal processing on the image signal input through the first transmission cable 6 (Step S116).

Thereafter, the image generation unit 92 generates the display image to be displayed in the display device 7 based on the image signal sequentially subjected to the signal processing by the signal processor 91 (Step S117), and outputs the display image to the display device 7 (Step S118). In this case, when a predetermined time (for example, 3 seconds) elapses after the select regions R1 to R9 are overlapped on the display image P1 displayed by the display device 7, the display controller 95a removes the select regions R1 to R9 from the display image P1 (non-display).

Subsequently, in a case where the display signal to display the select region on the display image P1 displayed by the display device 7 is input from the operation ring 51 or the input unit 52 (Step S119: Yes), the endoscope system 1 returns to Step S109. With this regard, in a case where the display signal to display the select region on the display image P1 displayed by the display device 7 is not input from the operation ring 51 or the input unit 52 (Step S119: No), the endoscope system 1 proceeds to Step S120.

In Step S120, in a case where the end signal to end the observation on the subject is input from the input unit 94 (Step S120: Yes), the endoscope system 1 ends this process. With this regard, in a case where the end signal to end the observation on the subject is not input from the input unit 94 (Step S120: No), the endoscope system 1 returns to Step S113.

In Step S110, in a case where the select signal to select any one of the plurality of select regions is not input from the operation ring 51 since the user performs the rotation operation on the operation ring 51 (Step S110: Yes), the endoscope system 1 proceeds to Step S119.

In Step S112, in a case where the determination signal to determine any one of the plurality of select regions is not input from the input unit 52 (Step S112: No), the endoscope system 1 proceeds to Step S119.

According to the first embodiment of the invention, the lens unit 53 is focused on at least one select region which is selected according to the operation of the operation ring 51 by the control of the AF controller 612 to drive the lens unit 53. Even in a region other than the center region in the display image P1, the other region is selected and the AF process is performed, so that the user can make the lens unit 53 focused on a user's desired region without changing the position of the insertion unit 2 (endoscope).

In addition, according to the first embodiment of the invention, the lens unit 53 is focused on at least one select region which is selected according to the operation of the operation ring 51 by the control of the AF controller 612 to drive the lens unit 53, so that the insertion unit 2 moves near to a portion of the subject where treatment is performed using a treatment tool, and there is no need to adjust the focus position. Therefore, it is possible to alleviate that the insertion unit 2 (endoscope) is contaminated or attached to an organ. Further, it is possible to reduce the procedure such as adjusting or moving the position of the insertion unit 2 (endoscope).

In addition, according to the first embodiment of the invention, the display controller 95a highlights the select region selected according to the select signal output by the operation ring 51. Therefore, the user can intuitively grasp the current select region.

In addition, according to the first embodiment of the invention, the select region is shifted to the other select region and highlighted whenever the display controller 95a outputs the select signal by the operation ring 51. Therefore, even the insertion unit 2 or the endoscope system 1 having less operation devices can easily change the select region with a simple operation.

In addition, in the first embodiment of the invention, the AF controller 612 controls the drive of the lens unit 53 to perform the AF process to make the lens unit 53 focused on at least one select region which is selected according to the operation of the operation ring 51. However, there may be performed a continuous AF process in which focusing is automatically kept while tracking the focus of the subject of at least one select region which is selected according to the operation of the operation ring 51.

Figure 8:
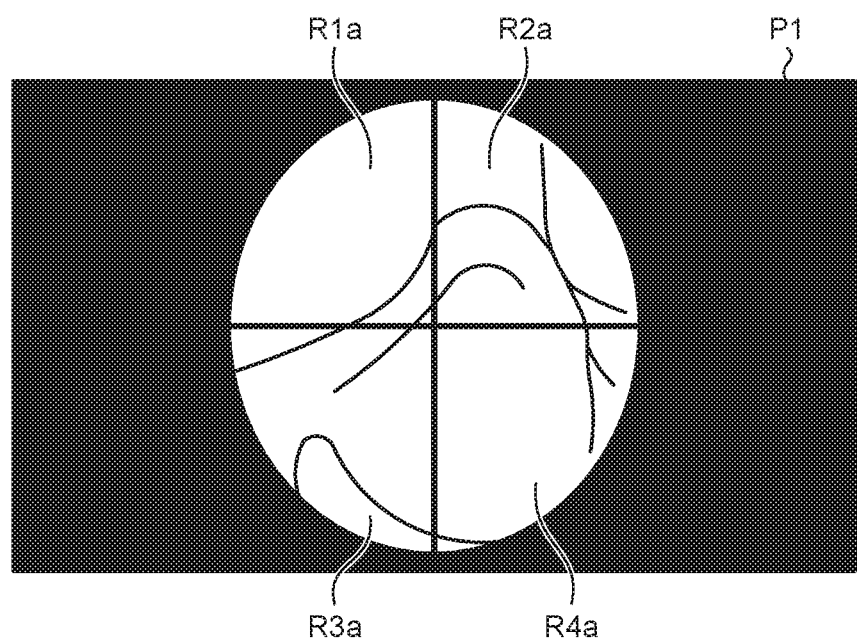
FIG. 8 is a diagram schematically illustrating another example of the plurality of select regions overlapped in the display image displayed by the display device according to the first embodiment of the invention.

Further, in the first embodiment of the invention, the display controller 95a overlaps the plurality of select regions R1 to R9 with a predetermined display size to the display image P1 which is displayed by the display device 7. However, when the display sizes of the select regions R1 to R9 may be appropriately changed. For example, as illustrated in FIG. 8, a plurality of select regions R1a to R4a may be displayed.

In addition, in the first embodiment of the invention, the display controller 95a overlaps nine select regions R1 to R9 on the display image P1. However, the number of select regions may be appropriately changed, and at least two or more regions may be overlapped.

In addition, in the first embodiment of the invention, the display controller 95a overlaps nine select regions R1 to R9 evenly on the display image P1 (a 3×3 matrix), but the invention is not limited thereto. The overlapping may be appropriately changed, and the regions may be overlapped in a cross shape for example.

In addition, in the first embodiment of the invention, the AF controller 612 performs the AF process of focusing the lens unit 53 on the select region which is selected by the operation ring 51, but the invention is not limited thereto. For example, the AF process may be performed to make the lens unit 53 focused on the select region which is selected according to the operation of the input unit 94 of the control device 9.

Second Embodiment

Next, a second embodiment of the invention will be described. In the first embodiment, the display controller overlaps the plurality of select regions onto the display image regardless of the type of the insertion unit (endoscope). However, in this second embodiment, the display sizes of the plurality of select regions overlapping onto the display image are changed according to the type of the insertion unit (endoscope). In the following, the configuration of the endoscope system according to this second embodiment will be described, and then the process performed by the endoscope system according to this second embodiment will be described. Further, the same configurations those of the endoscope system 1 according to the first embodiment will be attached with the same symbol, and the description will be omitted.

[Configuration of Endoscope System]

Figure 9:
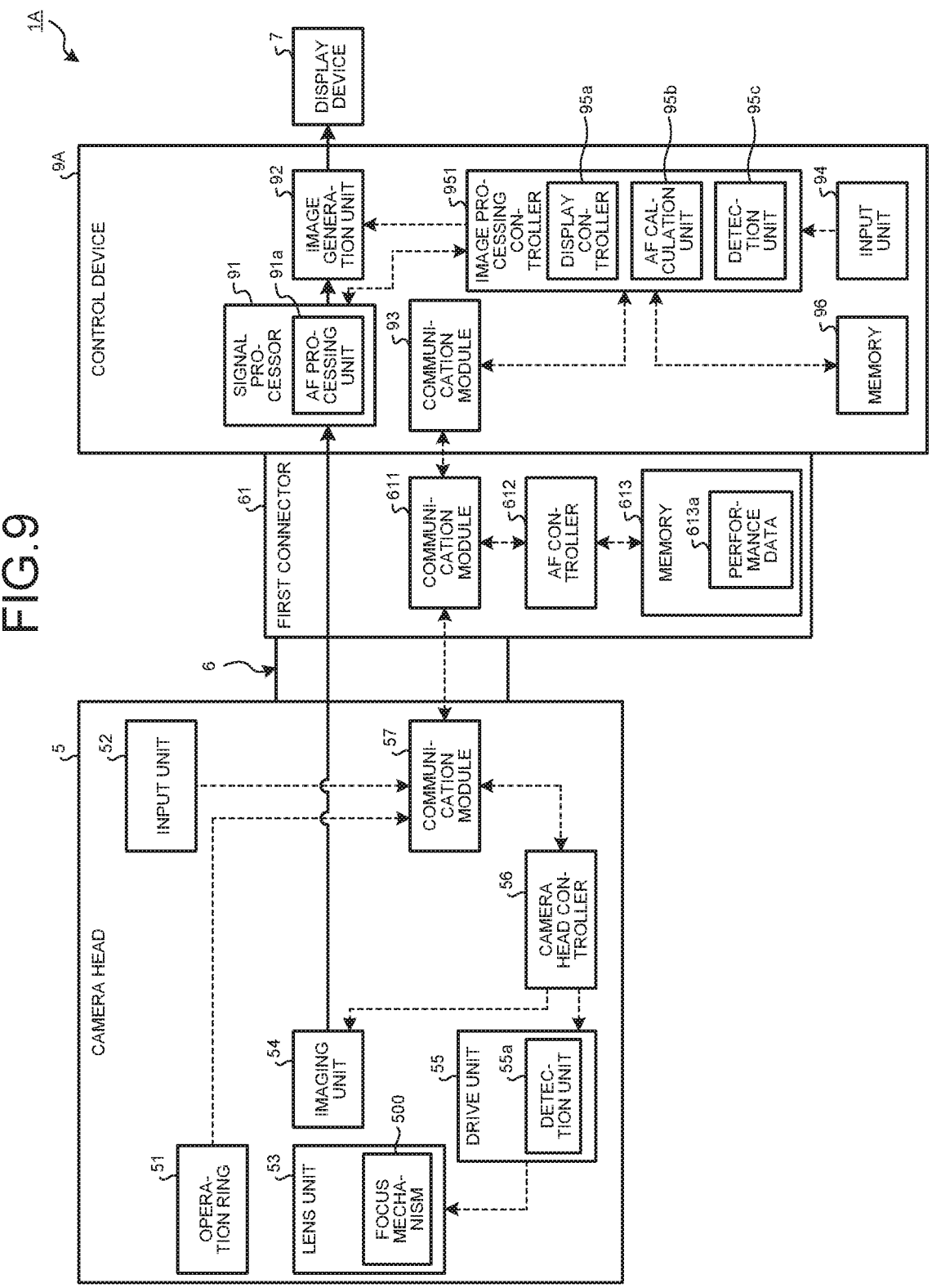
FIG. 9 is a block diagram illustrating a functional configuration of a camera head, a first connector, and a control device which are included in an endoscope system according to a second embodiment of the invention.

FIG. 9 is a block diagram illustrating a functional configuration of a camera head, a first connector, and a control device which are included in an endoscope system according to the second embodiment of the invention. An endoscope system 1A illustrated in FIG. 9 includes a control device 9A instead of the control device 9 according to the first embodiment. The control device 9A includes an image processing controller 951 instead of the image processing controller 95 according to the first embodiment.

Further, the image processing controller 951 includes a detection unit 95c in addition to the configuration of the image processing controller 95 according to the first embodiment.

The detection unit 95c detects the type of the insertion unit 2 (endoscope) connected to the camera head 5. Specifically, the detection unit 95c detects a boundary between the subject image (effective region) and a mask region other than the subject image contained in the display image based on a brightness signal (pixel value) of each pixel in the display image (video signal) generated by the image generation unit 92. The detection unit detects the type of the insertion unit 2 based on the detection result and type information indicating the position of the boundary of each insertion unit 2 (endoscope) recorded in the memory 96. Herein, the type information of the insertion unit 2 (endoscope) contains angle information indicating an angle of view and diameter information indicating the diameter of the insertion unit 2.

[Process of Endoscope System]

Next, the process performed by the endoscope system 1A will be described.

Figure 10:
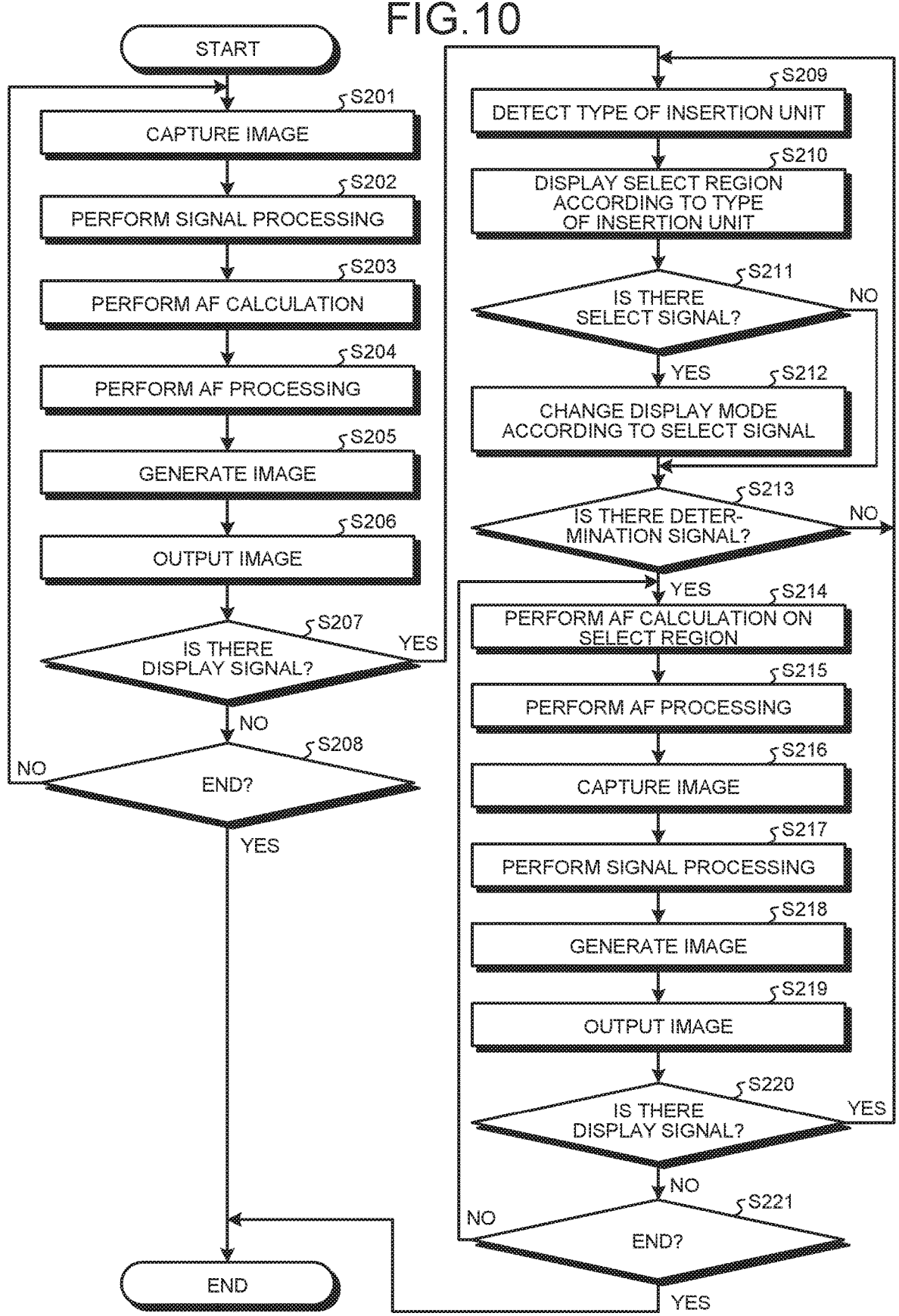
FIG. 10 is a flowchart illustrating the outline of a process performed by the endoscope system according to the second embodiment of the invention.

FIG. 10 is a flowchart illustrating the outline of the process performed by the endoscope system 1A. In FIG. 10, Step S201 to Step S208 and Step S211 to Step S221 correspond to Step S101 to Step S108 and Step S110 to Step S120 of FIG. 4 respectively, and the description will be omitted.

In Step S209, the detection unit 95c detects the type of the insertion unit 2 (endoscope) connected to the camera head 5. Specifically, the detection unit 95c detects the boundary between the subject image (effective region) contained in the display image and the mask region other than the subject image based on the brightness signal (pixel value) of each pixel in the display image (video signal) generated by the image generation unit 92. Then, the detection unit 95c detects the type of the insertion unit 2 based on the detection result and the type information indicating the position of the boundary of each insertion unit 2 (endoscope) recorded in the memory 96.

Figure 11A:
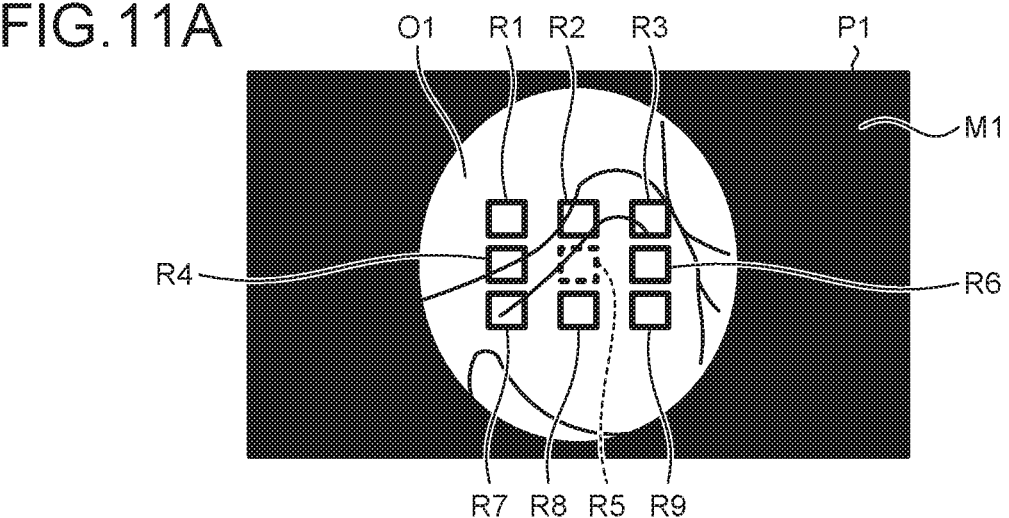
FIG. 11A is a diagram schematically illustrating an example of a plurality of select regions overlapped in the display image displayed by the display device according to the second embodiment of the invention.
Figure 11B:
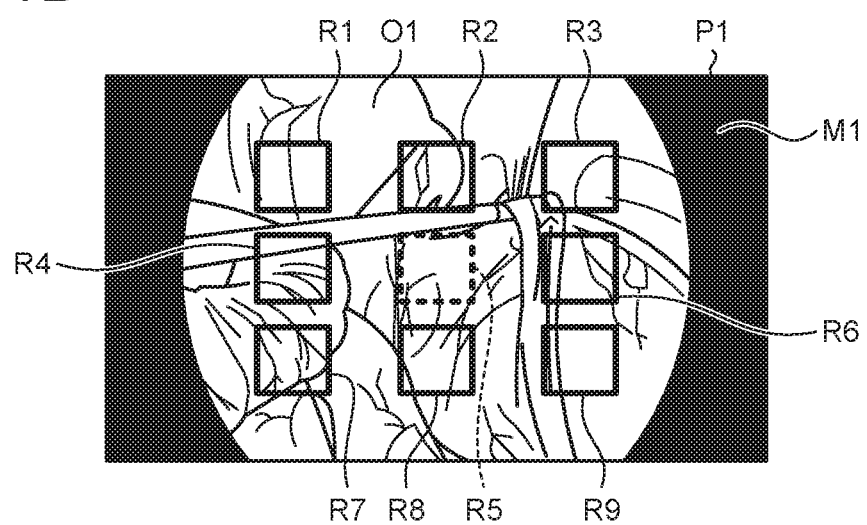
FIG. 11B is a diagram schematically illustrating another example of the plurality of select regions overlapped in the display image displayed by the display device according to the second embodiment of the invention.
Figure 11C:
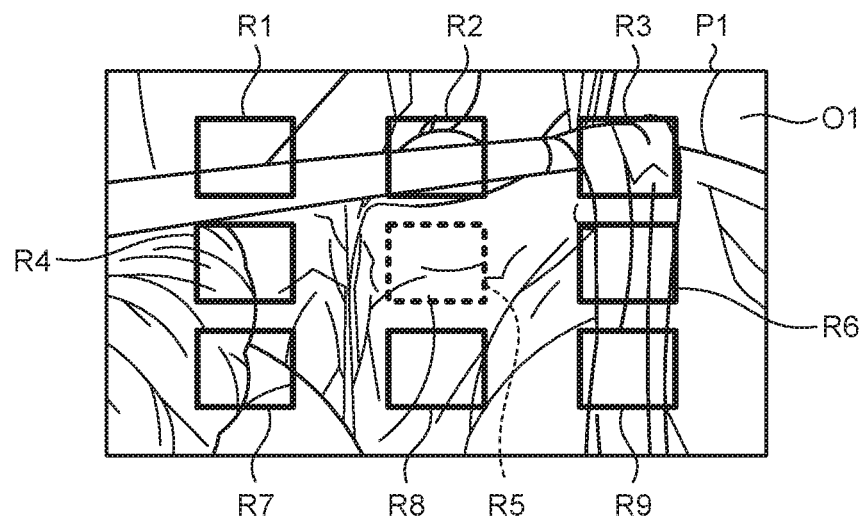
FIG. 11C is a diagram schematically illustrating another example of the plurality of select regions overlapped in the display image displayed by the display device according to the second embodiment of the invention.

Subsequently, the display controller 95a displays the select region on the display image P1 according to the type of the insertion unit 2 (endoscope) detected by the detection unit 95c (Step S210). Specifically, as illustrated in FIGS. 11A to 11C, the display controller 95a changes the display sizes of the plurality of select regions overlapped on the display image based on the type of the insertion unit 2 according to the boundary between the subject image detected by the detection unit 95c and the mask region other than the subject image, and displays the select regions in the display device 7. More specifically, as illustrated in FIGS. 11A to 11C, the display controller 95a changes the display sizes of the plurality of select regions R1 to R9 overlapped on the display image P1 based on a ratio between a display area of a subject image O1 and a display area of a mask region M1, and displays the select regions in the display device 7. For example, as illustrated in FIGS. 11A to 11C, the display controller 95a increases the display sizes of the plurality of select regions R1 to R9 overlapped on the display image P1 as the mask region M1 occupied in the display image P1 is decreased, and displays the select regions in the display device 7. After Step S210, the endoscope system 1A proceeds to Step S211.

According to the second embodiment of the invention, the same effects as those of the first embodiment are achieved, the display sizes of the plurality of select regions R1 to R9 overlapped on the display image P1 are changed according to the type of the insertion unit 2 (endoscope), and the select regions are displayed in the display device 7. Therefore, it is possible to display the plurality of select regions suitable to the insertion unit 2 in the display device 7.

Further, in the second embodiment of the invention, the detection unit 95c detects the boundary between the subject image contained in the display image and the mask region other than the subject image based on the brightness signal of each pixel in the display image, and detects the type of the insertion unit 2 based on the detection result and the type information indicating the position of the boundary of each insertion unit 2 recorded in the memory 96, but the invention is not limited thereto. A memory to record identification information (ID) for identifying the insertion unit 2 (endoscope) may be provided in the insertion unit 2 connected to the camera head 5, and the identification information is acquired from the memory so as to detect the type of the insertion unit 2 (endoscope). Of course, the detection unit 95c may detect the type of the insertion unit 2 based on input information which is input through the input unit 94 by the user.

In addition, in the second embodiment of the invention, the display controller 95a displays evenly the select regions R1 to R9 on the display image P1 regardless of whether a treatment tool is reflected on the display image P1. However, for example, the image generation unit 92 may detect the treatment tool using a well-known pattern matching to detect the treatment tool with respect to the display image P1, and may not display (remove) the select region with respect to the region where the treatment tool is reflected based on the detection result. Of course, the display controller 95a may display the select region to be overlapped with the distal end of the treatment tool detected by the image generation unit 92, and display the select region in the display device 7.

Third Embodiment

Next, a third embodiment of the invention will be described. In the first embodiment, the AF process is performed as a predetermined process on the select region selected by the user. However, an endoscope system according to the third embodiment performs a magnification process on the select region by performing an electronic zooming process. In the following, the configuration of the endoscope system according to the third embodiment is described, and then the process performed by the endoscope system according to the third embodiment will be described. Further, the same configurations those of the endoscope system 1 according to the first embodiment will be attached with the same symbol, and the description will be omitted.

[Configuration of Endoscope System]

Figure 12:
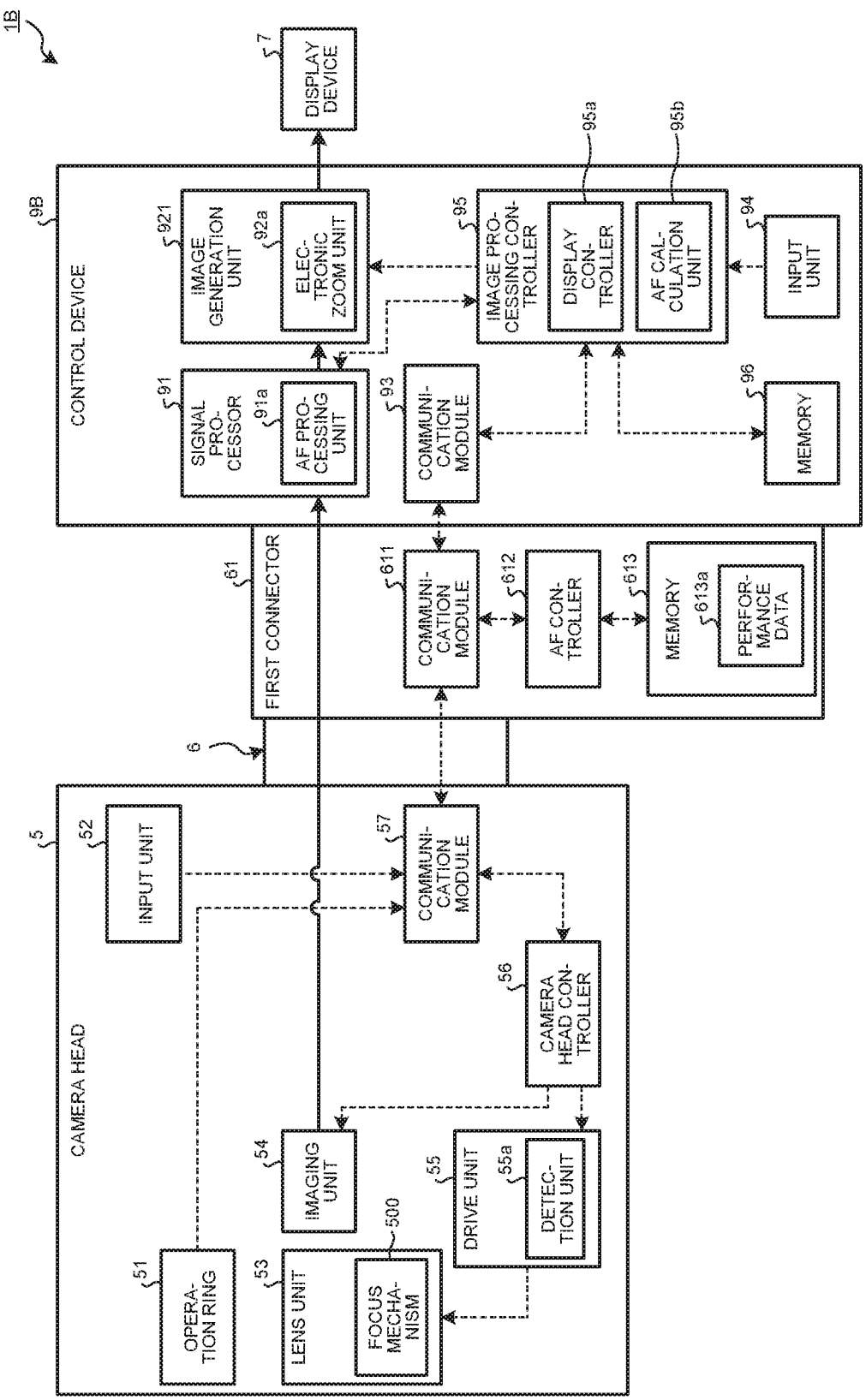
FIG. 12 is a block diagram illustrating a functional configuration of a camera head, a first connector, and a control device which are included in an endoscope system according to a third embodiment of the invention.

FIG. 12 is a block diagram illustrating a functional configuration of a camera head, a first connector, and a control device which are included in the endoscope system according to the third embodiment of the invention. An endoscope system 1B illustrated in FIG. 12 includes a control device 9B instead of the control device 9 according to the first embodiment. The control device 9B includes an image generation unit 921 instead of the image generation unit 92 according to the first embodiment.

The image generation unit 921 includes an electronic zoom unit 92a in addition to the configuration of the image generation unit 92 according to the first embodiment.

The electronic zoom unit 92a performs a trimming process (electronic zoom process) on the select region on the display image selected according to the select signal input from the operation ring 51 so as to resize the select region, and generates a magnification image obtained by magnifying the select region and outputs the image to the display device 7. Herein, the number of effective pixels of the magnification image is desirably 2 mega-pixels or more (for example, a so-called 2K resolution of 1920×1080 pixels).

[Process of Endoscope System]

Next, the process performed by the endoscope system 1B will be described.

Figure 13:
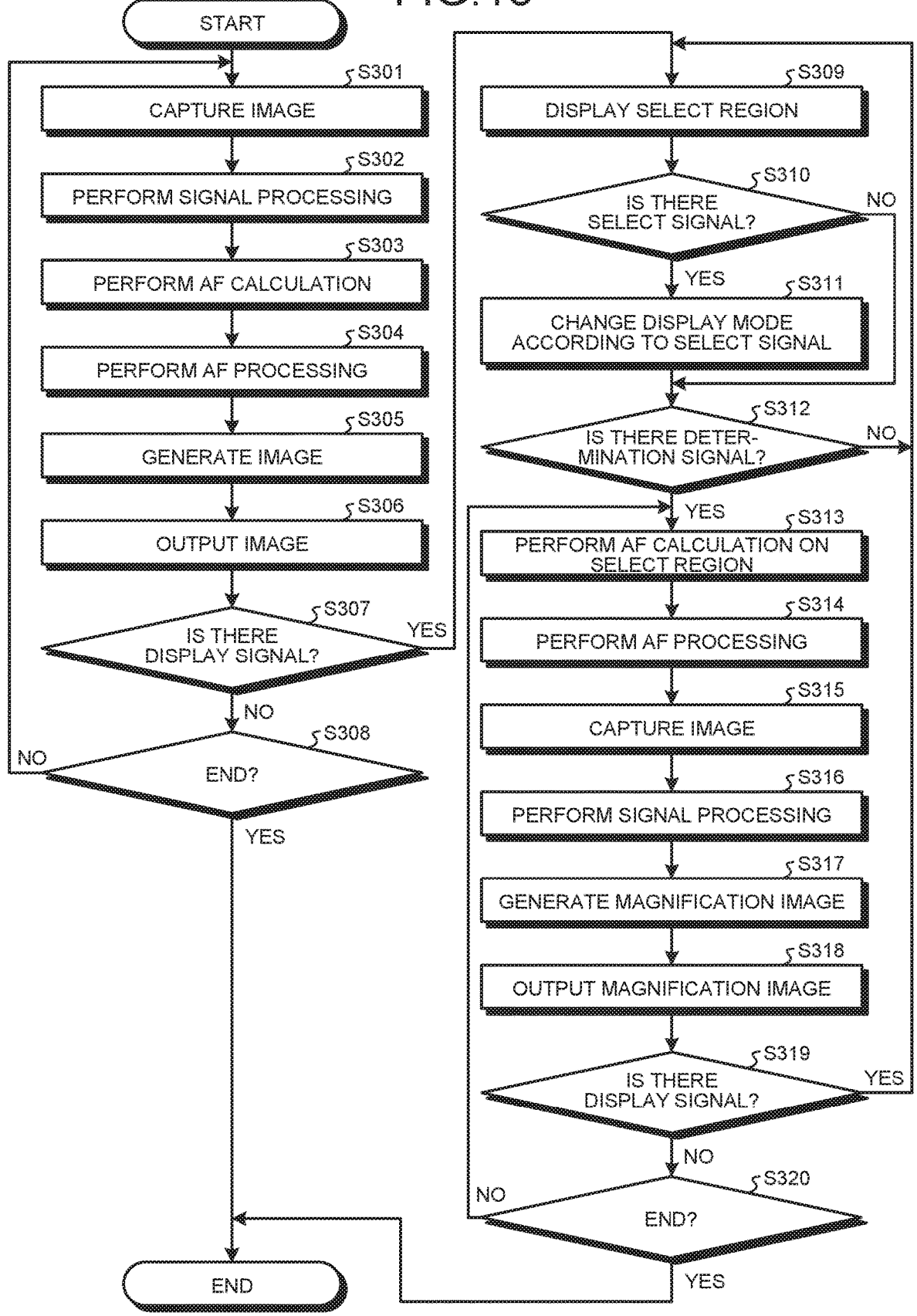
FIG. 13 is a flowchart illustrating the outline of a process performed by the endoscope system according to the third embodiment of the invention.

FIG. 13 is a flowchart illustrating the outline of the process performed by the endoscope system 1B. In FIG. 13, Step S301 to Step S316, Step S319, and Step S320 correspond to Step S101 to Step S116, Step S119, and Step S120 of FIG. 4 respectively.

Figure 14:
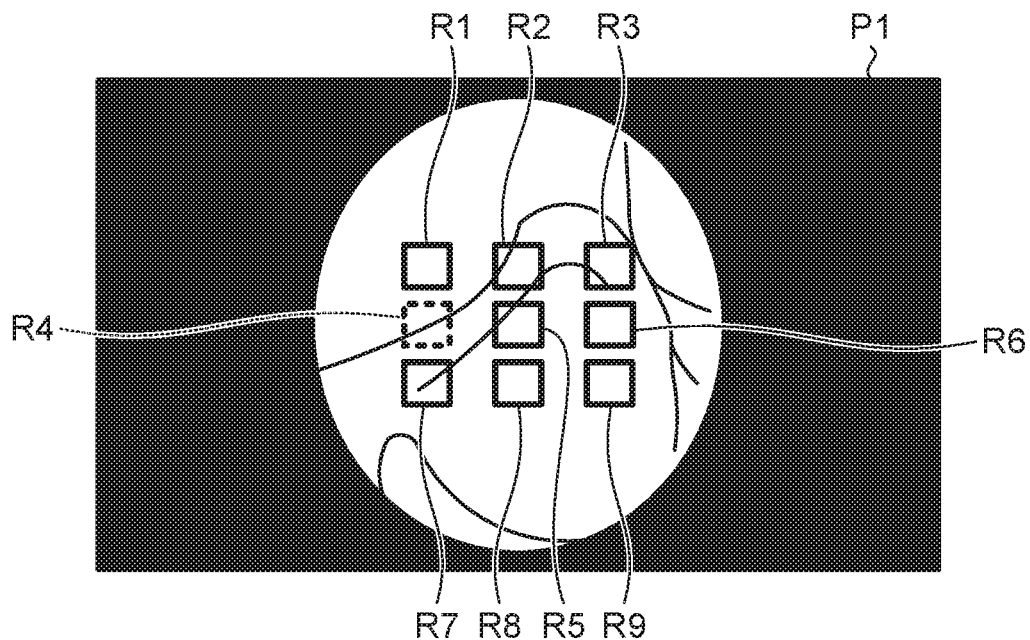
FIG. 14 is a diagram schematically illustrating an example of a plurality of select regions overlapped in the display image displayed by the display device according to the third embodiment of the invention.
Figure 15:
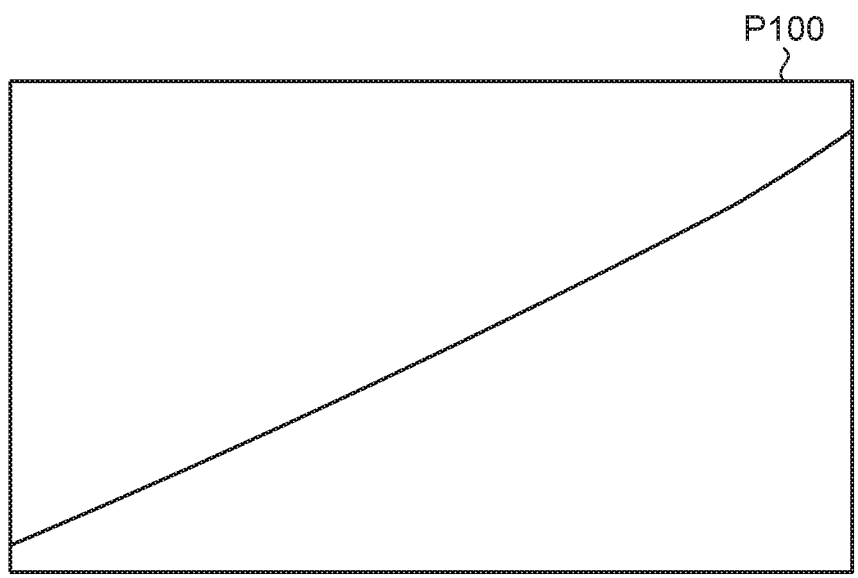
FIG. 15 is a diagram schematically illustrating an example of a magnification image of the select region of FIG. 14.

In Step S317, the image processing controller 95 causes the electronic zoom unit 92a to perform the trimming process (electronic zoom process) on the select region on the display image selected according to the select signal input from the operation ring 51 so as to generate a magnification image obtained by magnifying the select region. Specifically, as illustrated in FIGS. 14 and 15, in a case where the select region R4 on the display image P1 is selected according to the select signal input from the operation ring 51 (see FIG. 14), the electronic zoom unit 92a generates a magnification image P100 (see FIG. 15) obtained by performing the trimming process (electronic zoom process) on the select region R4 to magnify the select region.

Subsequently, the display controller 95a outputs the magnification image (video signal) generated by the electronic zoom unit 92a to the display device 7 (Step S318). With this configuration, the user operates the operation ring 51 to select any one or more of the select regions R1 to R9, and thus can check the magnification image P100 obtained by magnifying a desired region in the display device 7. In this case, the magnification image P100 causes the AF controller 612 to drive the lens unit 53 to perform the AF control on the select region R4 selected according to the select signal input from the operation ring 51, and thus becomes a focused image. In other words, the user can check the focused magnification image P100 by one operation in which the operation ring 51 is operated to select one of the select regions R1 to R9. After Step S318, the endoscope system 1B proceeds to Step S319.

According to the third embodiment of the invention, the electronic zoom unit 92a performs the electronic zoom process on the select region selected by the operation ring 51 even if the select region is other than the center region in the display image P1. Therefore, it is possible to magnify a user's desired position.

In addition, according to the first embodiment of the invention, the electronic zoom unit 92a performs the electronic zoom process on the select region selected by the operation ring 51 to magnify a user's desired position, so that the insertion unit 2 moves near to a portion of the subject where treatment is performed using the treatment tool, and there is no need to adjust the focus position. Therefore, it is possible to alleviate that the insertion unit 2 (endoscope) is contaminated or attached to an organ. Further, it is possible to reduce the procedure such as adjusting or moving the position of the insertion unit 2 (endoscope).

Further, in the third embodiment of the invention, the display controller 95a displays the select region R1 to R9 on the display image P1 by a predetermined size. For example, the plurality of select regions may be displayed by a display size such that the magnification image of the electronic zoom unit 92a becomes 2 mega-pixels or more.

Fourth Embodiment

Next, a fourth embodiment of the invention will be described. In the fourth embodiment, the illumination light emitted by the light source device 3 is adjusted by detecting a brightness of the select region. In the following, the configuration of an endoscope system according to the fourth embodiment will be described, and then the process performed by the endoscope system according to the fourth embodiment will be described. Further, the same elements of the endoscope system 1 according to the first embodiment will be indicated with the same symbol, and the description will be omitted.

[Configuration of Endoscope System]

Figure 16:
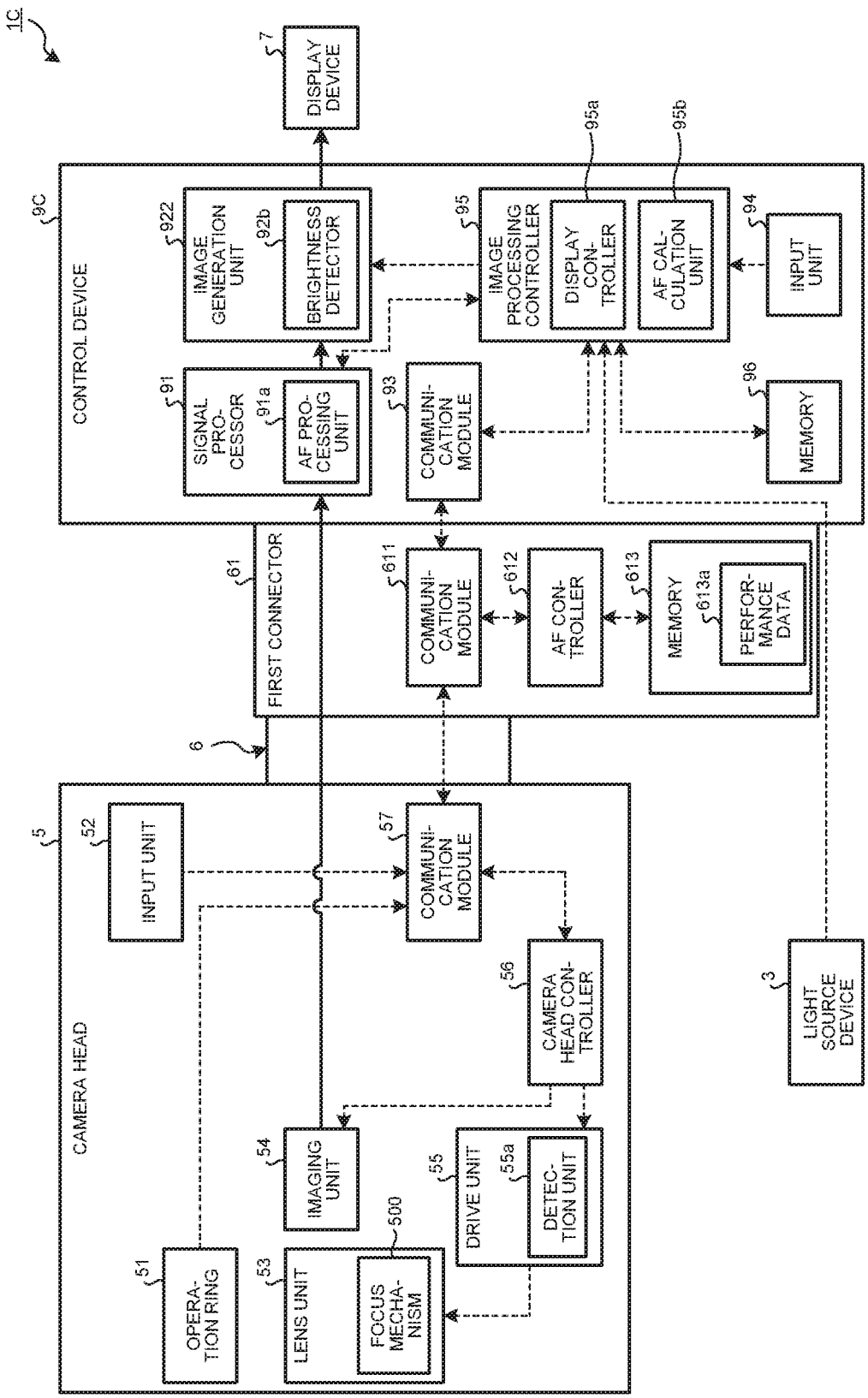
FIG. 16 is a block diagram illustrating a functional configuration of a light source device, a camera head, a first connector, and a control device which are included in an endoscope system according to a fourth embodiment of the invention.

FIG. 16 is a block diagram illustrating a functional configuration of a light source device, a camera head, a first connector, and a control device which are included in an endoscope system according to the fourth embodiment of the invention. An endoscope system 1C illustrated in FIG. 16 includes a control device 9C instead of the control device 9 according to the first embodiment. The control device 9C includes an image generation unit 922 instead of the image generation unit 92 according to the first embodiment.

The image generation unit 922 includes a brightness detector 92b in addition to the configuration of the image generation unit 92 according to the first embodiment.

The brightness detector 92b detects a brightness of the display image based on the brightness signal (pixel value) of each pixel in the display image (video signal), and generates a light control signal of the illumination light supplied by the light source device 3 based on the detection result. In addition, the brightness detector 92b detects the brightness of the select region on the display image selected according to the select signal input from the operation ring 51, and generates the light control signal of the illumination light emitted from the light source device 3 based on the detection result.

[Process of Endoscope System]

Figure 17:
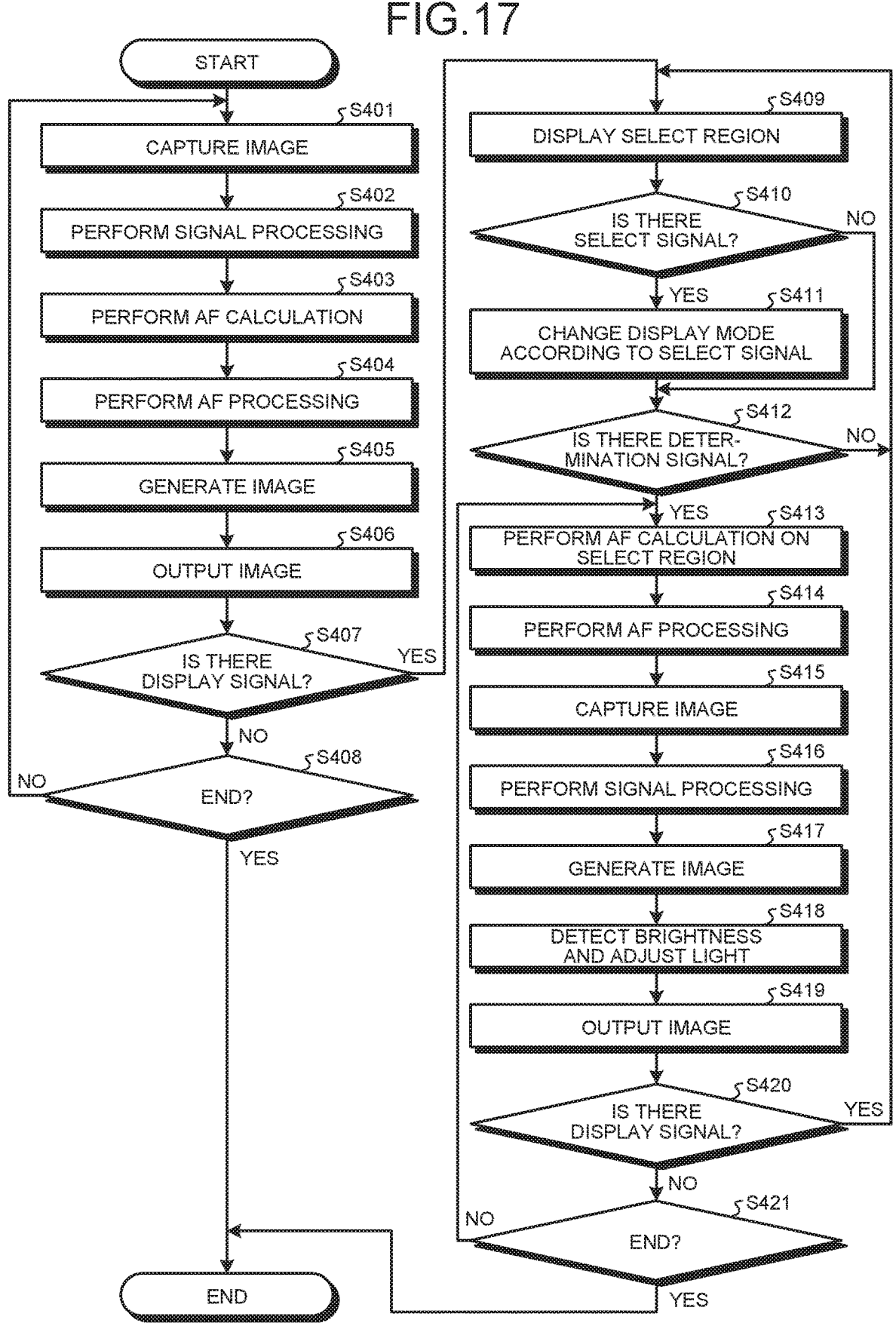
FIG. 17 is a flowchart illustrating the outline of a process performed by the endoscope system according to the fourth embodiment of the invention.

Next, a flowchart illustrating the outline of the process performed by the endoscope system 1C will be described. In FIG. 17, Step S401 to Step S417, and Step S419 to Step S421 correspond to Step S101 to Step S120 of FIG. 4 respectively.

In Step S418, the image processing controller 95 causes the brightness detector 92b to detect the brightness of the display image, and outputs the light control signal of the illumination light to the light source device 3 based on the detection result, so that the light source device 3 adjusts the illumination light. With this configuration, it is possible to supply the illumination light with a brightness suitable to a user's desired select region. After Step S418, the endoscope system 1C proceeds to Step S419.

According to the fourth embodiment of the invention, even if the select region is other than the center region in the display image P1, it is possible to select another region and adjust a brightness of a user's desired position.

Fifth Embodiment

Next, a fifth embodiment of the invention will be described. In the second embodiment, the endoscope system using a rigid endoscope (insertion unit 2) is applied to the invention. In the fifth embodiment, the invention is applied to a flexible endoscope which includes an endoscope device at the distal end of the insertion unit, and an endoscope system using a so-called video scope. Further, the same configurations those of the endoscope system 1 according to the first embodiment will be attached with the same symbol, and the description will be omitted.

[Configuration of Endoscope System]

Figure 18:
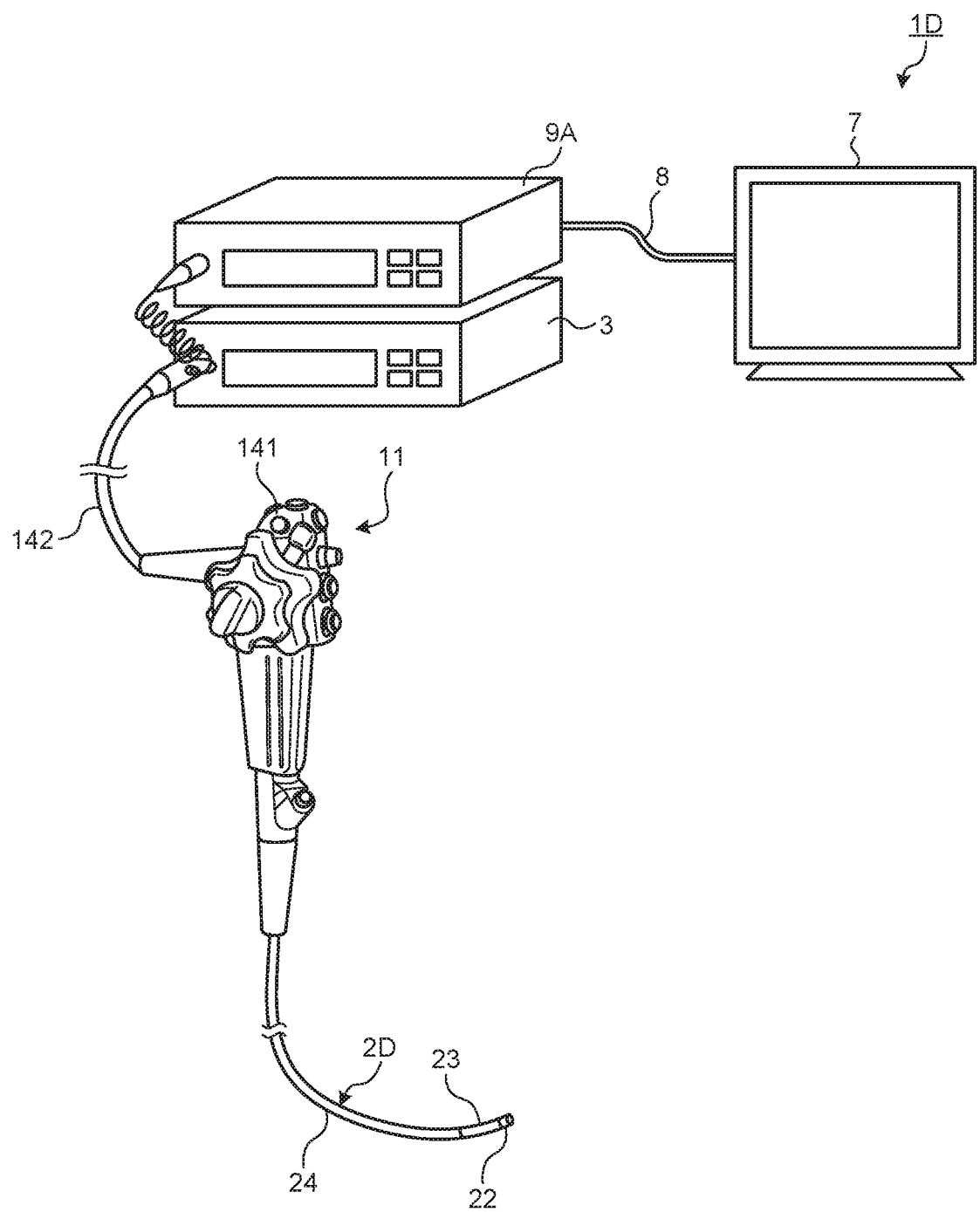
FIG. 18 is a diagram illustrating a schematic configuration of an endoscope system according to a fifth embodiment of the invention.

FIG. 18 is a diagram illustrating a schematic configuration of an endoscope system according to the fifth embodiment of the invention.

An endoscope system 1D illustrated in FIG. 18 includes an endoscope 11 which inserts an insertion unit 2D into an organ to capture an in-vivo image of an observed region of the subject and outputs the image signal, the light source device 3 which generates the illumination light emitted from the distal end of the endoscope 11, the control device 9A which processes the image signal output from the endoscope 11 to generate and output the display image, and the display device 7 which displays the display image.

As illustrated in FIG. 18, the endoscope 11 includes the insertion unit 2D which is formed in a flexible elongated shape, an operating unit 141 which is connected to a proximal end side of the insertion unit 2D and receives various operation signals, and a universal cord 142 which extends in a direction different from the extending direction of the insertion unit 2D from the operating unit 141, connected to the light source device 3 and the control device 9A, and includes various built-in cables including the first transmission cable 6.

As illustrated in FIG. 18, the insertion unit 2D includes a distal end portion 22 which includes the lens unit 53 (not illustrated) and the imaging unit 54 (not illustrated) built therein, a bent portion 23 which is connected to a proximal end side of the distal end portion 22 and is configured by a plurality of bent pieces in a freely bending manner, and a longitudinal flexible pipe 24 which is connected to a proximal end side of the bent portion 23 and is flexible. Then, the imaging unit 54 is provided in the distal end portion 22. The image signal captured by the imaging unit 54 is output to the control device 9A through the operating unit 141 and the universal cord 142 which includes the first transmission cable 6 built therein. In this case, the number of effective pixels of the imaging unit 54 (image sensor) is 2 mega-pixels or more (for example, a so-called 2K resolution of 1920× 1080 pixels).

According to the fifth embodiment of the invention, the same effects as those in the second embodiment are achieved even in a case where the flexible endoscope (an endoscope 11) is used.

Further, the fifth embodiment of the invention has been described about an example where the endoscope 11 is provided with the imaging unit 54 in a distal end portion 22 of the flexible insertion unit 2D. However, even a rigid endoscope equipped with the imaging unit in a rigid insertion unit can be applied. In this case, similarly to the imaging unit 54 of the fifth embodiment, the number of effective pixels of the imaging unit is desirably 2 mega-pixels or more (for example, a so-called 2K resolution of 1920×1080 pixels).

Other Embodiments

In the description of the process of the endoscope system in this specification, the context of steps is specified using the expressions "first", "thereafter", "subsequently", and "then". However, the order of steps necessary for executing the invention is not uniquely determined by these expressions. In other words, the order of the endoscope system described in this specification may be changed within a reasonable extent.

In addition, the invention is not limited to the above-described embodiments, but may specified by modifying the components within a scope not departing the spirit of the invention in a stage of implementation. In addition, the plurality of components disclosed in the embodiments may be appropriately combined to form various inventions. For example, some of the components described in the above-described embodiment may be omitted. Further, the components described in the respective embodiment may be appropriately combined.

In addition, terms referred with reference to terms which are referred in a wider or synonymous sense at least once in the specification or the drawings may be replaced with the different terms in any place in the specification and the drawings. In this way, various modifications and applications may be made within a range not departing from the spirit of the invention.

In this way, the invention may include various embodiments which are not described herein. Various design changes may be made within a range of technical ideas specified in claims.

REFERENCE SIGNS LIST 1, 1A, 1B, 1C, 1D ENDOSCOPE SYSTEM
2, 2D INSERTION UNIT
3 LIGHT SOURCE DEVICE
4 LIGHT GUIDE
5 CAMERA HEAD
6 FIRST TRANSMISSION CABLE
7 DISPLAY DEVICE
8 SECOND TRANSMISSION CABLE
9, 9A, 9B, 9C CONTROL DEVICE
10 THIRD TRANSMISSION CABLE
11 ENDOSCOPE
51 OPERATION RING
52 INPUT UNIT
53 LENS UNIT
d. 55a Detection Unit
54 IMAGING UNIT
55 DRIVE UNIT
56 CAMERA HEAD CONTROLLER
61 FIRST CONNECTOR
62 SECOND CONNECTOR
91 SIGNAL PROCESSOR
91a AF PROCESSING UNIT
92, 921, 922 IMAGE GENERATION UNIT
92a ELECTRONIC ZOOM UNIT
92b BRIGHTNESS DETECTOR
95, 951 IMAGE PROCESSING CONTROLLER
95a DISPLAY CONTROLLER
95b AF CALCULATION UNIT
95c DETECTION UNIT
96 MEMORY
141 OPERATING UNIT
500 FOCUS MECHANISM
612 AF CONTROLLER
M1 MASK REGION
O1 SUBJECT IMAGE
P1 DISPLAY IMAGE
P100 MAGNIFICATION IMAGE
R1 to R9, R1a to R4a SELECT REGION

The invention claimed is:

1. A control device, comprising:
circuitry configured to:
process an image signal generated by a camera to generate a display image to be displayed;

obtain a type of an endoscope coupled to the control device;

generate a plurality of select regions selectable according to an external operation, wherein a size of all select regions of the plurality of select regions is determined in accordance with the type of the endoscope;

overlap all of the plurality of select regions with the display image and output the overlapped image to a display; and perform a predetermined process on one selected region of the plurality of select regions, wherein the one selected region is selected according to the external operation and on less than an entirety of the image signal and not perform the predetermined process outside the one selected region of the plurality of select regions, such that at least one of a magnification and focus of the one selected region of the plurality of select regions in the display image is displayed.

2. The control device according to claim 1, wherein the circuitry is configured to move one or more of a plurality of lenses to focus on the one selected region selected according to the external operation.

3. The control device according to claim 1, wherein the circuitry is further configured to:
perform a trimming process on a predetermined region in the display image to generate a magnification image,
wherein the trimming process is performed on the one selected region selected according to the external operation to generate the magnification image.

4. The control device according to claim 1, wherein the circuitry is further configured to:
detect a brightness of an illumination light emitted from a light source based on a pixel value of a predetermined region in the display image to generate a light control signal to adjust the light source, and
detect wherein a brightness of the illumination light is detected with respect to the one selected region selected according to the external operation to generate the light control signal.

5. The control device according to claim 1, wherein the circuitry is configured to detect the type of the endoscope based on a boundary between a subject image and a mask region in the display image.

6. The control device according to claim 1, wherein the circuitry is further configured to:
output a select signal to select any one of the plurality of select regions, and
highlight the selected select region which is selected according to the select signal.

7. The control device according to claim 6, wherein the circuitry is configured to transition the selected select region to another selected select region and highlight the another selected select region whenever the select signal is output.

8. The control device according to claim 6, further comprising an operation ring provided rotatably about a predetermined axis, wherein the circuitry is configured to output the select signal at each predetermined rotation angle in response to rotation of the operation ring.

9. The control device according to claim 1, wherein the circuitry is configured to perform the predetermined process by:
magnifying one selected region of the plurality of select regions other than a center region selected according to the external operation and on less than an entirety of the image signal, and
outputting the magnified selected region to the display.

10. The control device according to claim 1, wherein the plurality of select regions are spaced apart from one another.

11. An endoscope system, comprising:
an endoscope configured to be inserted in a subject;
a display; and
a camera to receive a subject image formed by the endoscope to perform a photoelectric conversion to generate an image signal;
circuitry configured to:
process the image signal to generate a display image;
output the display image to the display;
obtain a type of the endoscope;
generate a plurality of select regions selectable according to an external operation, wherein a size of all select regions of the plurality of select regions is determined in accordance with the type of the endoscope;
overlap all of the plurality of select regions with the display image and output the overlapped image to a display; and
perform a predetermined process on one selected region of the plurality of select regions, wherein the one selected region is selected according to the external operation and on less than an entirety of the image signal and not perform the predetermined process outside the one selected region of the plurality of select regions, such that at least one of a magnification and focus of the one selected region of the plurality of select regions in the display image is displayed.

12. The endoscope system according to claim 11, wherein the circuitry is configured to:
output a select signal to select any one of the plurality of select regions, and
highlight the selected select region selected according to the select signal.

13. The endoscope system according to claim 12, wherein the circuitry is configured to transition the selected select region to another selected select region and highlight the another selected select region whenever the select signal is output.

14. The endoscope system according to claim 12, further comprising an operation ring provided rotatably about an axis perpendicular to a light-receiving surface of the camera, wherein the circuitry is configured to output the select signal at each predetermined rotation angle in response to rotation of the operation ring.

15. The endoscope system according to claim 11, further comprising:
a camera head to which the endoscope is detachably connected,
wherein the camera head includes the camera, and
wherein number of effective pixels of the camera is 8 mega-pixels or more.

16. The endoscope system according to claim 11,
wherein the endoscope includes an elongated shape to be inserted to the subject,
wherein the camera is provided in a distal end portion of the elongated shape, and
wherein the number of effective pixels of the camera is 2 mega-pixels or more.

17. The endoscope system according to claim 11,
wherein a monitor size of the display is 31 inches or more.

18. A processing method, comprising:
processing an image signal generated by a camera to generate a display image to be displayed;
obtaining a type of an endoscope coupled to the camera;
generating a plurality of select regions selectable according to an external operation, wherein a size of all select regions of the plurality of select regions is determined in accordance with the type of the endoscope;

performing a predetermined process on one selected region of the plurality of select regions selected according to an external operation and on less than an entirety of the image signal; and not performing the predetermined process outside the one selected region of the plurality of select regions, such that at least one of a magnification and focus of the one selected region of the plurality of select regions in the display image is displayed.

19. The processing method according to claim 18, wherein performing the predetermined process includes:

magnifying one selected region of the plurality of select regions other than a center region selected according to the external operation and on less than an entirety of the image signal, and outputting the magnified selected region to the display.

20. The processing method according to claim 18, wherein the plurality of select regions are spaced apart from one another.

21. A non-transitory computer readable medium having stored thereon a program that, when executed by a computer, causes the computer to execute processing, the processing comprising:

processing an image signal generated by a sensor to generate a display image to be displayed;

obtaining a type of an endoscope coupled to the sensor;

generating a plurality of select regions selectable according to an external operation, a size of all select regions of the plurality of select regions is determined in accordance with the type of the endoscope;

performing a predetermined process on one selected region of the plurality of select regions, wherein the one selected region is selected according to an external operation and on less than an entirety of the image signal; and not performing the predetermined process outside the one selected region of the plurality of select regions, such that at least one of a magnification and focus of the one selected region of the plurality of select regions in the display image is displayed.

22. The non-transitory computer readable medium according to claim 21, wherein performing the predetermined process includes:

magnifying one selected region of the plurality of select regions other than a center region selected according to the external operation and on less than an entirety of the image signal, and outputting the magnified selected region to the display.

23. The non-transitory computer readable medium according to claim 21, wherein the plurality of select regions are spaced apart from one another.

\* \* \* \* \*